United States Patent [19]

Itami et al.

[11] Patent Number: 5,039,630
[45] Date of Patent: Aug. 13, 1991

[54] METHOD FOR PRODUCING GRANULAR MULTI-CELLULAR GLASS AND THE GLASS PRODUCED BY THE METHOD

[75] Inventors: Hiroshi Itami, Yokohama; Akira Nagara; Hiroshi Taguchi, both of Takasaki; Takashi Ehara, Tokyo, all of Japan

[73] Assignee: Kirin Beer Kabushiki Kaisha, Tokyo, Japan

[21] Appl. No.: 649,216

[22] Filed: Jan. 25, 1991

Related U.S. Application Data

[63] Continuation of Ser. No. 372,163, Jun. 27, 1989, abandoned, which is a continuation of Ser. No. 139,645, Dec. 30, 1987, abandoned.

[30] Foreign Application Priority Data

Jan. 14, 1987 [JP] Japan .................. 62-6802
Oct. 6, 1987 [JP] Japan ................ 62-250665

[51] Int. Cl.$^5$ .............. C03C 15/00; C03B 19/00
[52] U.S. Cl. ........................... 501/39; 65/22; 65/31; 210/500.26
[58] Field of Search ............ 65/21.4, 22, 31, 30.12, 65/30.13, 22; 210/500.26; 501/39

[56] References Cited

U.S. PATENT DOCUMENTS

| | | | |
|---|---|---|---|
| 2,500,801 | 3/1950 | Church | 65/31 X |
| 3,843,341 | 10/1974 | Hammel et al. | 65/31 X |
| 3,904,422 | 9/1975 | Eaton | 65/31 X |
| 3,945,816 | 3/1976 | Johnson | 65/31 X |
| 4,052,010 | 10/1977 | Baker et al. | 241/20 |
| 4,234,330 | 11/1980 | Taupin et al. | 65/21 |
| 4,545,797 | 10/1985 | Elattar | 65/31 X |
| 4,657,875 | 4/1987 | Nakashima et al. | 65/31 X |
| 4,661,138 | 4/1987 | Murakami | 65/31 X |

FOREIGN PATENT DOCUMENTS

0117484 9/1984 European Pat. Off. .
58-60634 4/1983 Japan .
2151610 7/1985 United Kingdom .

OTHER PUBLICATIONS

"Effect of Conditions for Producing Ultrafiltration Membranes from Porous Glass . . . " Ermakova et al., Chemical Abstracts, vol. 103, No. 6, 1985.
"Silicate-Based Foaming Composition for Light-Weight Bldg. Material", Nakazaki et al., Chemical Abstracts, vol. 91, No. 22, 1979.
"Water-Insoluble Shaped Water Glass Foam", Kavoda, Chemical Abstracts, vol. 85, No. 6, Aug. 1976.
"Inorganic Foam Useful as Bldg. Material", Takahashi, Chemical Abstracts, vo. 84, No. 26, Jun. 1976.

*Primary Examiner*—Robert L. Lindsay
*Attorney, Agent, or Firm*—Ladas & Parry

[57] ABSTRACT

Disclosed is a granular multi-cellular glass and a method for producing the same. An ordinary multi-cellular glass grain having relatively low moisture content ratio was prepared as starting material. The glass grain is then dipped in water or alkali solution for eluting or dealkali treatment. By the dipping, soluble alkali components are mainly eluted from a surface layer and cell walls of the glass grain. Thus produced multi-cellular glass grain provides increased moisture content ratio because of the formation of micropores at the layer and cell wall portions. Disclosed also are controls of physical properties of the multi-cellular glass grain for controlling specific gravity, pore volume and pore diameter thereof. By these controls, resultant glass grain is provided with desirable physical properties available for a microcarrier for immobilizing microbe therein.

6 Claims, 13 Drawing Sheets

PULVERIZED GLASS PARTICLE DIAMETER OF RAW GLASS MATERIAL ($\mu$)

| SODA-LIME GLASS | $\overline{X}$ | $\overline{U}$ |
|---|---|---|
| GLASS GRAIN A | 30.0 | 50.0 (EXAMPLE 7) |
| GLASS GRAIN B | 16.1 | 12.5 (EXAMPLE 11) |

METHOD FOR PRODUCING GRANULAR MULTI-CELLULAR GLASS AND THE GLASS PRODUCED BY THE METHOD

This application is a continuation of application Ser. No. 07/372,163, filed June 27, 1989 which is a continuation of Ser. No. 07/139,645, filed Dec. 30, 1987, both abandoned.

BACKGROUND OF THE INVENTION

The present invention relates to a method for producing a granular multi-cellular glass (foam glass) and such granular multi-cellular glass produced by the method. More specifically, the present invention relates to a method for producing such glass having high moisture content ratio or water absorption ratio and to a granular multi-cellular glass produced thereby. The present invention also relates to a method for controlling physical properties of the glass and to a granular multi-cellular glass obtained by the control of physical properties thereof.

Granular multi-cellular glass or porous glass grain is light in weight and provides heat insulative characterisitics. Further, the glass generally provides low moisture content ratio or low water absorbing property, and is non-combustible with high moldability. Therefore, the granular multi-cellular glass has been widely available for building materials.

Such granular multi-cellular glass is produced by, for example, injecting gas into molten glass, or by adding and mixing foaming agent with the molten glass and rapidly cooling the mixture by dropping the mixture into cooling medium as described in Japanese Patent Publication No. 51-18968. Alternatively, such glass is produced by the steps of pulverizing glass, adding foaming agent such as carbonate, nitrate and carbon into the pulverized glass, granulating or pelletizing the mixture to a predetermined size, and heating the granulations at a temperature of about from 800° to 1100° C.

Cell size in the granular cellular glass is controllable by controlling distribution of sizes of pulverized glass particles and kind and amount of the foaming agents. Further, final grain diameter of the granular glass is also controllable by controlling cooling temperature for the molten foaming glass, granullation or pelletization degree, and heating temperature, etc.

In this case, the heating temperature is higher than the softening temperature of the glass (about from 710° to 730° C. at which the glass has Poise viscosity of $5 \times 10^7$). Therefore, the glass hardly provides water permeability, and almost all blisters or seeds in the glass are independent cells (closed cells). As a result, resultant granular multi-cellular glass provides water absorption or moisture content ratio of only from 5 to 20% (vol %) after the glass is at a reduced pressure atmosphere and is subjected to water absorption. In this connection, the glass is usable and applicable to a heat insulating member.

Here, the other types of utility and applicability would be conceivable in the granular multi-cellular glass if moisture content ratio thereof is increased or controlled, and if other physical properties of the glass is controllable. In this connection, various invesitigations have been conducted to increase moisture content ratio of the glass. Through researches and experiments, moisture content ratio has been increased to about 20 to 50% by adding excessive amount of foaming agent to the glass powders, or by adding 5 to 20% of silica sand or diatomaceous earth.

However, thus obtained product is not uniform in its gravity and moisture content ratio and provides low compression strength and low chemical stability.

Throughout the specification and claims, various physical properties are described. The followings are the definitions of these properties:

[moisture content or water absorption ratio] (%): $X/Y$ in which,

X: water volume absorbed in the granular multi-cellular glass (porous glass grain) which is dipped in water at vacuum pressure (about 76 mm Hg) for about 10 minutes, and then at normal atmospheric pressure.

Y: volume of porous glass grain which volume includes volume of pores in which no water is absorbed therein within 1 minute dipping in water at atmospheric pressure.

[porosity] $X/Y$ in which,

X: volume of mercury filled in the pores of the porous glass grain at pressure starting from vacuum pressure and ending on 30,000 PSIa by mercury injecting method.

Y: volume of porous glass grain which volume includes volume of pores in which no mercury is filled even at the pressure of 30,000 PSIa.

[bulk specific gravity] $X/Y$ in which

X: total weight of porous glass grains accumulated in a cylindrical member,

Y: internal volume of the cylindrical member

[apparent specific gravity] $X/Y$ in which

X: weight of a porous glass grain in air,

Y: volume of the porous glass grain which volume includes the volume of all pores;

[absolute specific gravity]

This specific gravity excluding pore portions in the porous glass grain. The absolute specific gravity is equal to (apparent specific gravity)/(1-porosity)

[median pore diameter] ($\mu$m)

Each of the pores provides its pore internal volume. The total pore volumes are integrated, and the integrated volume is divided by two. A specific pore diameter corresponding to the half integrated volume is sought. This specific pore diameter is referred to as median pore diameter. In the specification, mercury pressure is increased from vacuum pressure to 30,000 PSIa in mercury injecting method. Increased mercury volumes (intrusion volume into pores) are plotted, with respect to each of the diameters of the pores. Then total volume is divided into two having equal volume to each other. The pore diameter at which the two equal volumes can be defined is referred to as the median pore diameter.

[specific gravity in water]

Specific gravity of the porous glass grain in which water absorbing portions is excluded. That is, weight of the glass grain is divided by apparent volume which volume excludes water volume contained in the glass. The specific gravity in water is equal to (apparent specific gravity)/(1−moisture content ratio),

[apparent specific gravity in water]

Apparent specific gravity of the porous glass grains which contain water therein. The apparent specific gravity in water is equal to (apparent specific gravity) plus (moisture content ratio)

[pore volume (Hg intrusion volume)] (ml/g)

Volume of pores in the porous glass grain having 1 gram in weight. In the present invention, the volume is represented by mercury injecting amount into the pores when the mercury pressure increases from its vacuum pressure to 30,000 PSIa by mercury injection method.

SUMMARY OF THE INVENTION

It is therefore, an object of the present invention to overcome the above-described drawbacks and to provide an improved granular multi-cellular glass or porous glass grain and a method for producing the same.

Still another object of the present invention is to provide such multi-cellular glass grain and the production method thereof in which resultant glass grain has high moisture content ratio with improved fluid permeability and retainability.

Still another object of this invention is to provide such glass grain and its production method in which effective liquid can be retained in the glass for a long period of time.

Still another object of this invention is to provide a microcarrier formed of the improved multi-cellular glass grain, which microcarrier is capable of immobilization of microbes with sufficient mechanical strength and durability.

Still another object of this invention is to provide an improved multi-cellular glass grain and its production method in which physical properties of the glass such as specific gravity and median pore diameter are controllable.

These and other objects of the present invention will be attained by the steps of preparing multi-cellular glass grain having a surface layer and internal cell walls as a starting material having relatively low moisture content ratio, dipping the glass grain in one of water and alkali solution, and eluting primarily soluble alkali component from the surface layer and the cell walls so as to form micropores in the layer and cell wall. This elution treatment (or hereinafter can be referred to dealkalization or "alkali decreasing" treatment) generates the micropores or pinholes to change originally closed cells into open cells, and increases diameters of the micropores or pinholes already formed, to thus increase fluid permeability and moisture content ratio, yet also increasing fluid retainability. If liquid such as perfume, fertilizer and herbicide are impregnated in such glass, long term service life results because of the prolonged fluid retainability.

Further, according to the present invention, various physical properties of the multi-cellular glass are controllable. That is, in the present invention, the multi-cellular glass is produced by the steps of (1) provisionally obtaining a group of graphical curves each showing the relationship between a specific gravity and a median pore diameter using various pelletized particle diameter as parameters, the particles being obtained by pulverization of a raw glass material, (2) determining desirable specific gravity and median pore diameter (as desirable factors) of a final glass product and delineating a curve which passes through a point determined by these desirable factors, the delineated curve being analogous or parallel with the group of curves; (3) selecting desirable particle diameter which corresponds to the delineated curve; (4) preparing a multi-cellular glass grain by employing a raw material glass having thus selected particle diameter, and heating the glass grain at a condition the same as in the production of glasses which constitute said group of curves, thus prepared glass grain having a surface layer and internal cell walls; (5) dipping thus prepared glass grain in one of water and alkali solution for eluting (or dealkalization) treatment, and (6) controlling at least one of temperature of water and the alkali solution, pH of the alkali solution and period of the dipping for eluting primarily soluble alkali components from the surface layer and the cell walls, so that desirable specific gravity and desirable median pore diameter are simultaneously obtained in the final multi-cellular glass. By the control of at least one of temperature of one of water and alkali solution, pH of the alkali solution and dipping period for elution, moisture content ratio of the glass is controlled, so that median pore diameter and specific gravity thereof are also controllable.

By this control, optimum pore dimension is provided which is capable of being used as a microcarrier for immobilizing microorganism therein. To be more specific, when the multi-cellular glass grain having moisture content ratio not less than 50% is provided, such glass grain is particularly available for immobilization of yeast for the production of alcoholic drinks. These and other objects of the present invention will become more apparent from the following description and accompanying drawings.

DETAILED DESCRIPTION OF THE PREFERRED EMBODIMENTS

Figure 1:
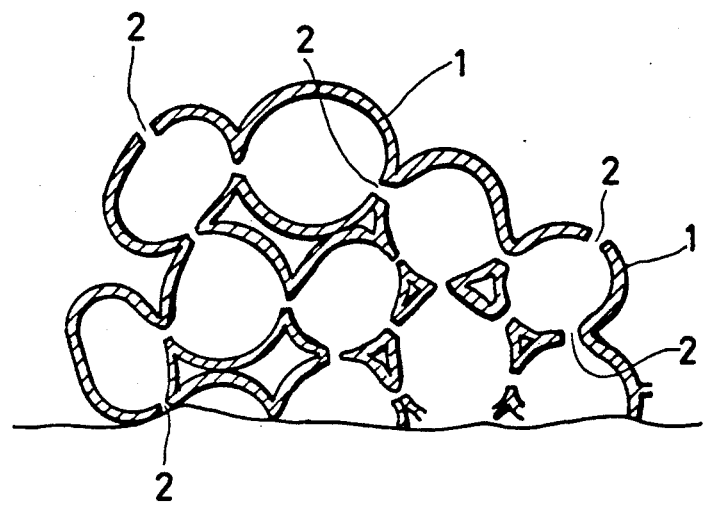
FIG. 1 is a schematic view showing blisters or cells of a multi-cellular glass grain after elution or dealkalization treatment.

Analized first is the components eluted from the granular multi-cellular glass (porous glass grain) by dealkalization treatment. Prepared were soda-lime glasses and borosilicate glass having the compositions shown in Table 1. The glasses were pulverized so as to have average particle diameter and particle diameter deviations described in Table 1, and the particles were used as raw materials and porous glass samples A-1 through A-4 were obtained each having 100 grams in weight.

Each of the samples was dipped in 1000 ml of ion-exchanged water having temperatures for given periods those shown in Table 2, and eluted components were analyzed by atomic absorption spectrometry. Analyzed components are shown in Table 2.

As is apparent from Table 2, non-alkali components such as $SiO_2$ and $Al_2O_3$ were found in addition to alkali components such as $Na_2O$, $K_2O$ and $CaO$, and eluted amounts were changed in accordance with dipping conditions and particle diameters of the glass raw materials. However, elution amount of alkali components is far greater than that of non-alkali components in view of the original glass powder components shown in Table 1. Therefore, by the eluting treatment, it is confirmed that eluted components are mainly alkali components.

Various examples according to the present invention will be described.

EXAMPLE 1

Prepared was a soda-lime glass having compositions shown in Table 1 below. The glass was subjected to levigation or elutriation for 10 hours to provide glass powders whose average particle dimater was 30 μm and the deviation value of the diameter was 50 μm, and 2% of $CaCO_3$ was added as a foaming agent to the glass powders, and the mixture was pelletized. The pelletized mixture was heated at a temperature of 850° C. for 100 seconds. Thus prepared sample has an average grain diameter of approximately 5 mm, and size of the blisters was in a range of from 0.02 mm to 0.05 mm. This sample was dipped in hot water having a temperature of 70° C. for 8 days.

Table 3 shows changes of chemical compositions of the sample before and after dealkalization treatment. Further, Table 4 shows changes of the physical properties of the sample before and after the dealkalization treatment. In Table 4, moisture content ratio is measured. For the measurement, 5 ml of the sample was provisionally placed in an aspiration filtering bottle having an internal volume of 1 l, and the sample was subjected to decompression for 10 minutes by a vacuum pump, and thereafter, water was poured into the bottle. Further, with respect to the moisture content ratio, volume of the granular multi-cellular glass was measured by a pycnometer for preparing 5 ml of glass, and the glass was put in an aspirating flask for sucking air in blisters of the glass for 10 minutes under vacuum. Thereafter, water was poured to allow water to be absorbed into the blisters. Absorbed water volume was measured, and ratio of this water volume to the glass volume was represented by percentagewise. Furthermore, compression strength was shown by mean or average value (e,ovs/x/ ) and its deviation value ($\sigma$) in Table 4.

As is apparent from Table 3, because of the eluting treatment, $Na_2O$ is particularly eluted from the glass sample rather than other components. Therefore, the eluting treatment can be referred to dealkalization or alkali decreasing treatment..

According to the Table 4, because of the dealkalization treatment, bulk specific gravity of the sample is lowered by 0.07 (from 0.155 to 0.148), and when the granular glasses were accumunated in a container having internal volume of 1 l, the total glass weight was reduced by 7 grams (from 155 g to 148 g), and absolute specific gravity of the glass is reduced by 0.01 (from 0.26 to 0.25). Because of these changes, moisture content ratio is increased by 65% (from 10.2% to 75.2%).

In view of the foregoing, when dealkalization treatment is applied to the granular multi-cellular glass, eluted are alkalic components in a surface layer of the multi-cellular glass and peripheral walls of respective cells 1 thereof as shown in FIG. 1. By the elution and at the eluted portions, pin holes or micropores 2 are formed, through which water enters the respective cells 2. More specifically, in the elution treatment, sodium ion is released from the multi-cellular glass walls into the hot water, and the sodium hydroxide is provided by the reaction of sodium ion with water. Therefore, the walls of the multi-cellular glass are subjected to erosion by the sodium hydroxide and the hot water. As a result, described as hereinafter, moisture content ratio and specific gravity in water are remarkably increased. On the other hand, compression strength is slightly lowered by the dealkalization treatment.

Figure 2A:
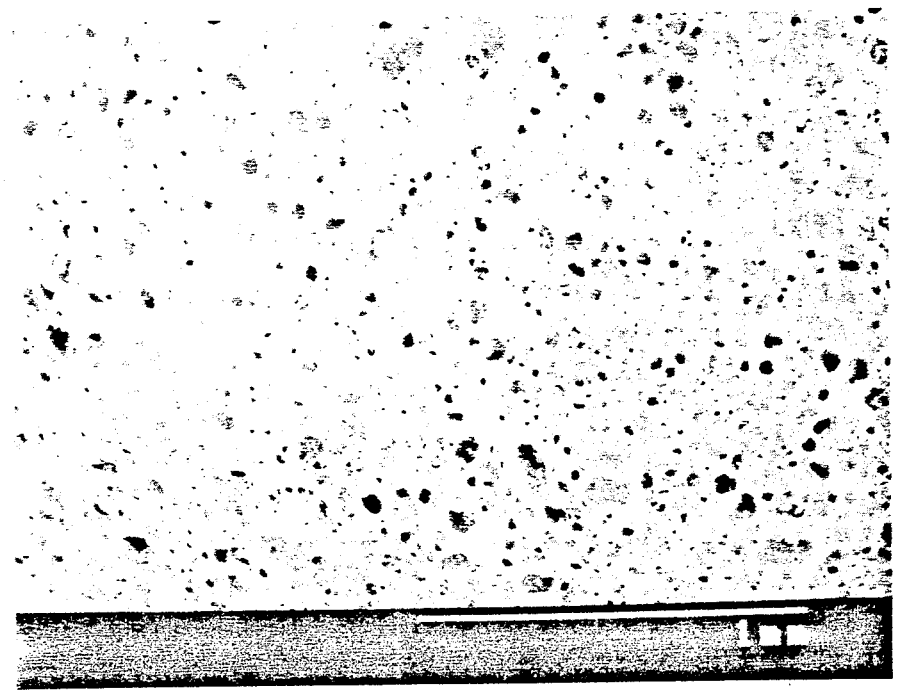
FIG. 2(a) is a microscopic photograph showing a surface layer of a granular multi-cellular glass before its dealkalization treatment.
Figure 2B:
FIG. 2(b) is a microscopic photograph showing a surface layer after dealkalization treatment.

FIGS. 2(a) and 2(b) are microscopic phtographs showing a surface layer of the granular multi-cellular glass having a grain diameter of 3 mm. In the Figures, FIG. 2(a) shows the state before dealkalization treatment and FIG. 2(b) after dealkali treatment. The glass before the dealkalization treatment has a moisture content ratio of 13% at its surface layer portion. However, as shown in FIG. 2(b), great number of pin holes are formed after the dealkalization treatment, and moisture content ratio is increased to 73%.

Figure 3A:
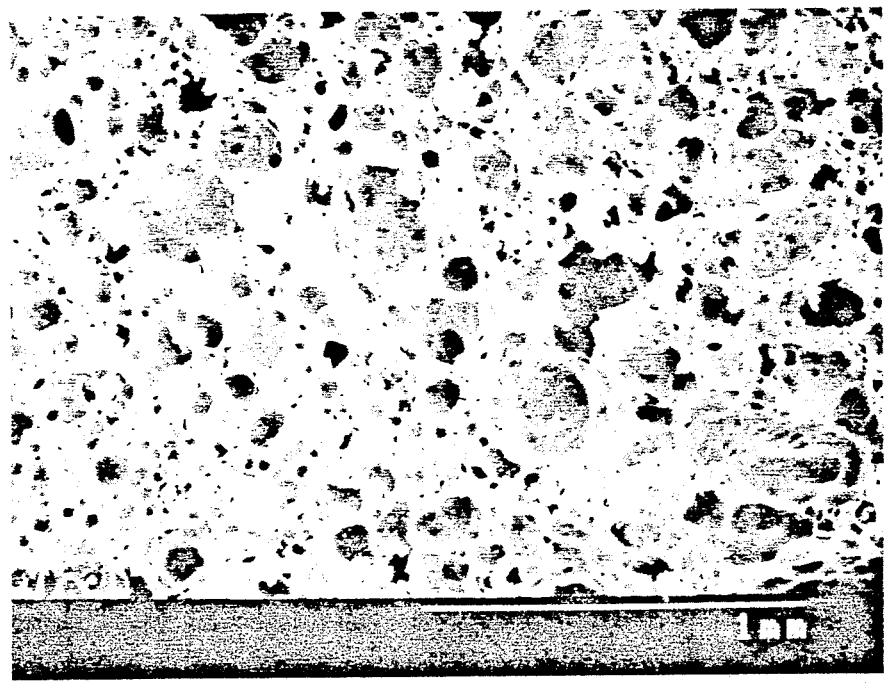
FIGS. 3(a) and 3(b) are microscopic photographs showing cross-sectional structure of the glass shown in FIGS. 2(a) and 2(b), and FIGS. 3(a) and 3(b) show states before and after the dealkalization treatment, respectively.
Figure 3B:

FIGS. 3(a) and 3(b) are microscopic phtographs showing cross-sectional structure of the glass shown in FIGS. 2(a) and 2(b). (FIGS. 3(a) and 3(b) show states before and after the dealkalization treatment.) According to the Figures, large number of pin holes are formed in the glass after the dealkalization treatment. It has been also found that increase in pin hole numbers at the surface layer portion of the glass is higher than that at the internal portion thereof.

This increase in moisture content ratio implies high water retention in the independent cells of the granular glass. Further, thus formed pin holes 2 have extremely small diameters, so that free water discharge from the cells are restrained once the water is entered into the independent cells through the pin holes. As a result, resultant granular multi-cellular glass has improved water retainability.

EXAMPLE 2

Figure 4:
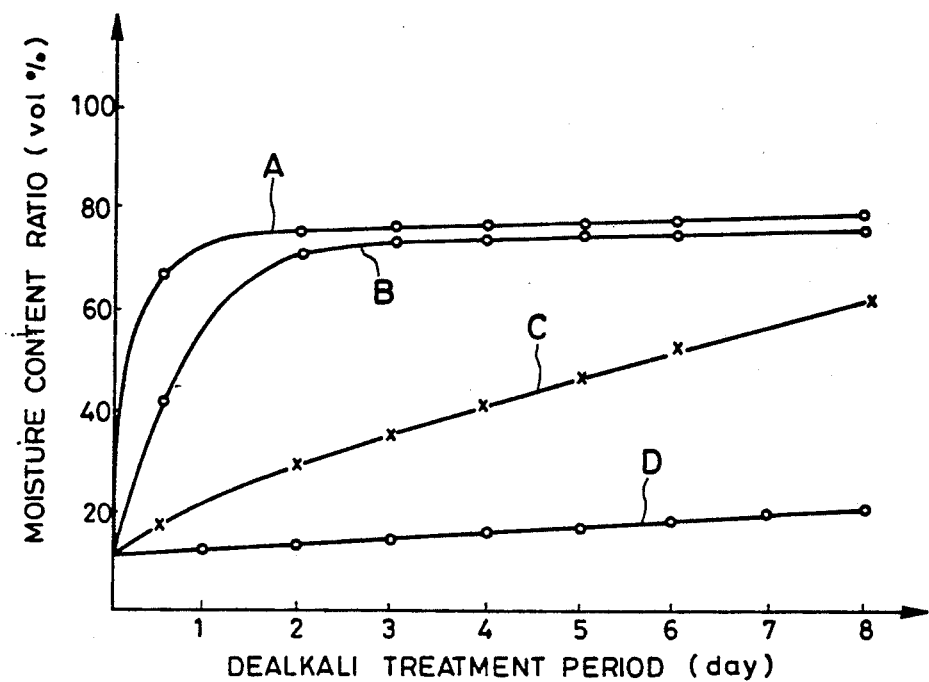
FIG. 4 is a graphical representation showing the relationship between dealkalization treatment period and moisture content ratio.

In the above-described Example 1, glass sample is dipped in hot water for the dealkalization treatment. However, the dealkalization treatment is also performed by dipping the glass sample in alkali solution. Prepared were four samples each having chemical compositions the same as that shown in Table 3, and the four samples had initial physical properties the same as one another. Two samples were dipped in sodium carbonate solution ($Na_2CO_3$), and remaining two samples were dipped in water. Changes in moisture content ratio with respect to processing periods are shown in FIG. 4.

(1) Initial physical properties of the four granular multi-cellular glass samples are as follows:

| | |
|---|---|
| Bulk specific gravity | 0.24 |
| Apparent specific gravity | 0.38 |
| Moisture content ratio | 11,5% |
| (maximum moisture content ratio | 84.8%) |
| [maximum moisture content ratio, $\frac{0.38}{2.5} = 84.8\ (\%)$ | (2.5 is absolute specific gravity of solid glass) |
| diameter of glass grain | from 4.0 to 6.0 mm |
| (average diameter | 5 mm) |

(2) Explanation of Curves A through D

| | |
|---|---|
| Curve A-$Na_2CO_3$ 5% solution | 70° C. |
| Curve B-$H_2O$ | 70° C. |
| Curve C-$Na_2CO_3$ 5% solution | 25° C. |
| Curve D-$H_2O$ | 25° C. |

According to the experiments, high moisture content ratio of the glass is obtainable when the glass is dipped in the alkali solution rather than dipped in water. Further, increased moisture content ratio is obtainable if the solution temperature is high. In case the solution temperature is rather low (25° C.), moisture content ratio is gradually improved with time (see curves C and D of FIG. 4). On the other hand, if the solution temperature is high (70° C.) moisture content ratio is rapidly increased to 70 to 80% for only two days dipping, and thereafter, the increase is almost stopped (see curves A and B). Incidentally, caustic soda is also applicable as alkali dipping solution.

EXAMPLE 3

Figure 5:
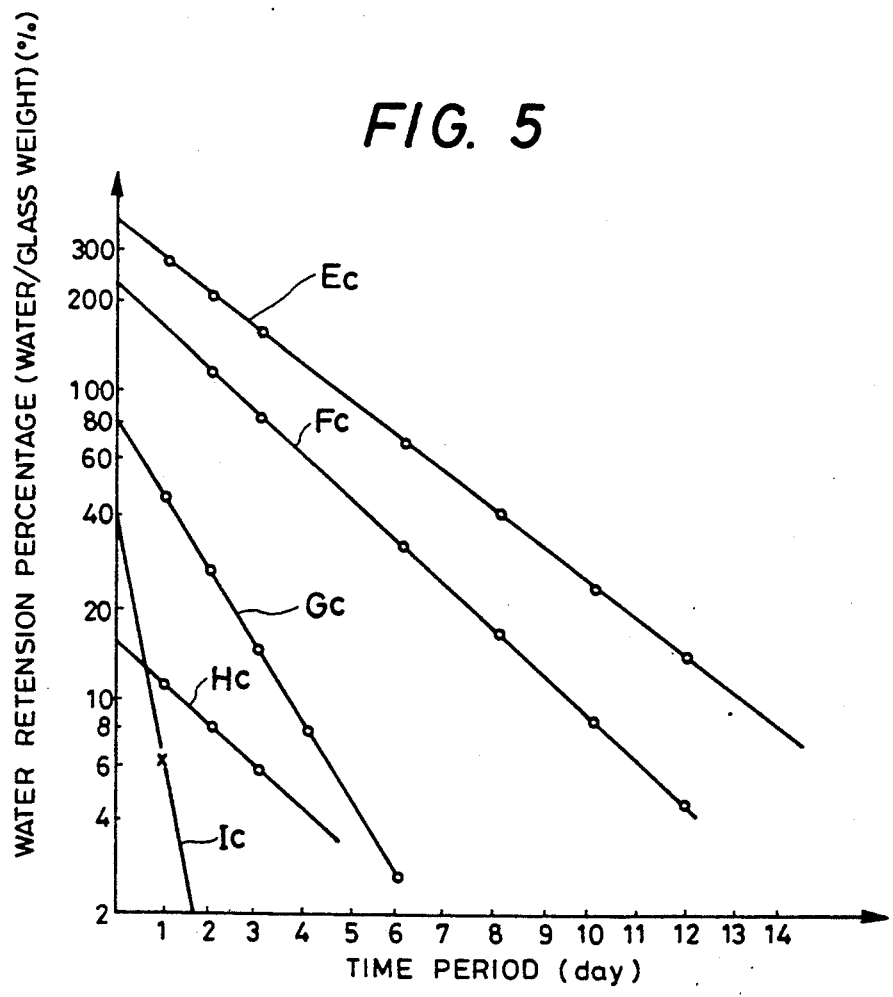
FIG. 5 is a graph showing the relationship between the time period and water retaining ratio.

Prepared were five samples each having average grain diameter of 5 mm. Samples E, F, G and H were granular multi-cellular glasses each having chemical compositions the same as that shown in Table 3. Samples E-H were processed to provide physical properties different from one another. The sample I was a clay ball. These samples were subjected to decompression, and water was absorbed in these samples. Thereafter, these samples were placed in a beaker at ambient temperature of 30° C. and humidity of 70%. Water retention ratio with time were measured with respect to these samples. The water retention percentage is percentile ratio of water weight retained in the sample to weight of the sample at its drying state. Test results are shown in FIG. 5.

| | Physical properties | | | |
|---|---|---|---|---|
| | bulk specific gravity | apparent specific gravity | moisture content ratio (vol %) | Curves |
| Glass sample E | 0.09 | 0.16 | 82.6 | Ec |
| Glass sample F | 0.14 | 0.26 | 79.4 | Fc |
| Glass sample G | 0.21 | 0.36 | 48.8 | Gc |
| Glass sample H | 0.20 | 0.37 | 13.3 | Hc |
| Clay ball I | 0.64 | 1.28 | 39.8 | Ic |

According to the experiments, it is apparent that the samples having high moisture content ratio (samples E and F) provided prolonged water retainability such as about 12 to 14 days, while the samples having low moisture content ratio (sample I-clay ball) rapidly discharged water therefrom for about 1.5 days. That is, the samples E and F provided their maximum water absorbing amounts about 5 to 6 times as large as the maximum water absorbing amount of the clay ball I, and the sampels E and F provided water retaining period of about 10 times as large as that of the clay ball.

EXAMPLE 4

In this Example 4, median pore diameter, pore volume (Hg intrusion volume) and moisture content ratio were primarily investigated in the porous or multi-cellular glasses. Prepared were two samples (granular multi-cellular glasses) formed of soda-lime glasses and two samples (granular multi-cellular glasses) formed of borosilicate glasses. Chemical compositions of these glasses are shown in Table 5. With respect to the total four samples, physical properties before and after the dealkalization treatment were measured, and results are shown in Table 6. For the dealkalization treatment, regarding the soda-lime glasses (samples 1-A and 2-A in Table 6), the glasses were dipped in hot water contained in an autoclave having a temperature of 120° C. for 4 hours, and regarding the borosilicate glasses (samples 1-B and 2-B), these were dipped in hot water containing 5% of sodium carbonate ($Na_2CO_3$) contained in an autoclave having a temperature of 120° C. for 4 hours. In the experiments, absolute specific gravity was measured by pycnometer method, and moisture content ratio was measured by the method described in EXAMPLE 1. Median pore diameter was measured by injecting mercury under pressure (for example, by employing mercury porosimeter) into the pores of the glasses, and more specifically, by using Simazu's poresizer 9305 (product of Micrometric Co., Ltd., U.S. company).

Figure 6:
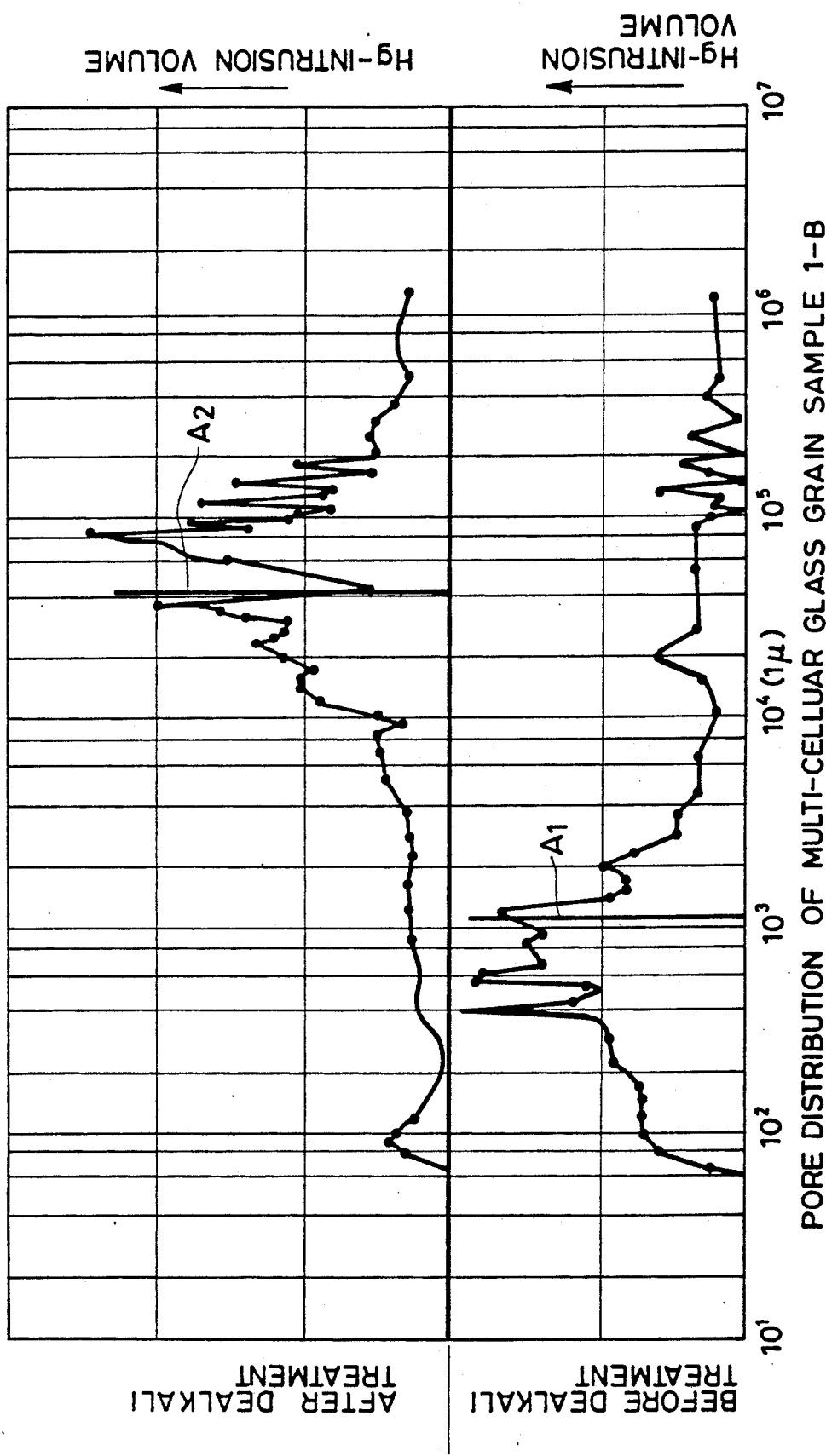
FIG. 6 is a graph showing distribution of pore diameters before and after the dealkalization treatment.

FIG. 6 shows distributions of pore diameters in the sample 1-B shown in Table 6 before and after the dealkalization treatment. In the graphical representations, mercury was successively injected into the porous glass sample, and pore volume relative to each of the pore diameters was presented in an ordinate. In FIG. 6, the lines A1 and A2 divides the totally integrated area into two regions having areas equal to each other, and the pore diemater size at the line designates the median pore diameter. More specifically, the mercury porosimeter originally defines correspondence between the mercury injection pressures and pore diameters. Mercury is injected under pressure into the porous sample at a first pressure, and total mercury intrusion volume V1 is measured. In case of the small pores, mercury cannot be sufficiently injected thereinto, and in the next step, mercury is again injected into the porous glass sample at a second pressure higher than the first pressure. Then the total mercury intrusion volume V2 is measured. Thereafter, (V2−V1) is calculated for plotting the difference (V2−V1) in the ordinate of FIG. 6. Such procedure is successively carried out in accordance with every increased mercury pressures, and plotted are (Vn−Vn−1), - - - (V3−V2), (V2−V1), and V1 as ordinates. These all differences are integrated. (This integrated volumes is equal to Vn). The integrated volume (integrated area in FIG. 6) is divided into two having volumes (areas) equal to each other by a vertical line A1 (or A2). The vertical line passes through a one specific pore diameter in an abscissa in FIG. 6. This pore diameter is referred to "median pore diameter".

As is apprent from FIG. 6, median pore diameters of the sample 1-B before and after the dealkalization treatment were 0.11 μm (abscissa value at the line A1), and 4.16 μm (abscissa value at the line A2), respectively. Therefore, the median pore diameter was remarkably increased by the dealkalization treatment. Further, according to Table 6, moisture content ratio and median pore diameter are critically changed by the dealkalization treatment, and it would be understood that the change in median pore diameter is approximately proportional to the change in moisture content ratio.

EXAMPLE 5

In this example, confirmed was the control of pore distribution and moisture content ratio by controlling temperatures and density of the dipping liquid and by controlling dipping period. In order to conduct the experiments, prepared were Sample I (clay ball) and four samples E, F, G and H those having the chemical compositions the same as those in EXAMPLE 3. These samples had grain diameters of 5 mm. In these samples, absolute specific gravity, moisture content ratio, porosity and median pore diameter were different from one another as shown in Table 7, and experimental results are shown in FIG. 5 in which water was absorbed in the respective samples and water retention percentages were obtained in such a manner the same as that of Example 3.

According to FIG. 5 and Table 7, absolute specific gravities were gradually increased from sample E to sample H, and reversely, moisture content ratio, porosity, pore volume and median pore diameter were gradually decreased from the samples E to sample H.

Further, according to FIG. 5, prolonged water retainability was obtained in case of the porous carriers (multi-cellular glass) having high moisture content ratio (samples E and F), while water retention percentage was promptly decreased in case of the clay ball (sample I) inspite of the fact that it provided initial water moisture content ratio higher than that of the sample H.

In view of the above, by lowering absolute specific gravity and by increasing moisture content ratio, porosity and pore volumes of the granular multi-cellular glass, water retainability is considered to be improved. The porous glass having small median pore diameter like the sample H can provide low water discharge speed. However, such glass is not capable of wide range utility since its initial moisture content ratio is low.

EXAMPLE 6

Other types of porous carriers each having physical properties different from one another were prepared for testing water retention percentages. Prepared were four granular multi-cellular glass samples M, N, O and P, and inorganic carriers such as chamotte (sample Q), anthracite (sample R) and CB filtering member (chemical bacteriological filter sample S). Samples M and N were formed of borosilicate glass whose compositions were the same as that shown in Table 5, and samples O and P were formed of sodalime glass shown in Table 5. Each of the samples had 5 grams in weight, and was placed in a beaker having an internal volume of 100 ml, under an ambient temperature of 15° C. and humidity of 50% so as to measure water retaining percentages in each of the samples. Physical properties of these samples are shown in Table 8, and test results are shown in FIG. 7.

Figure 7:
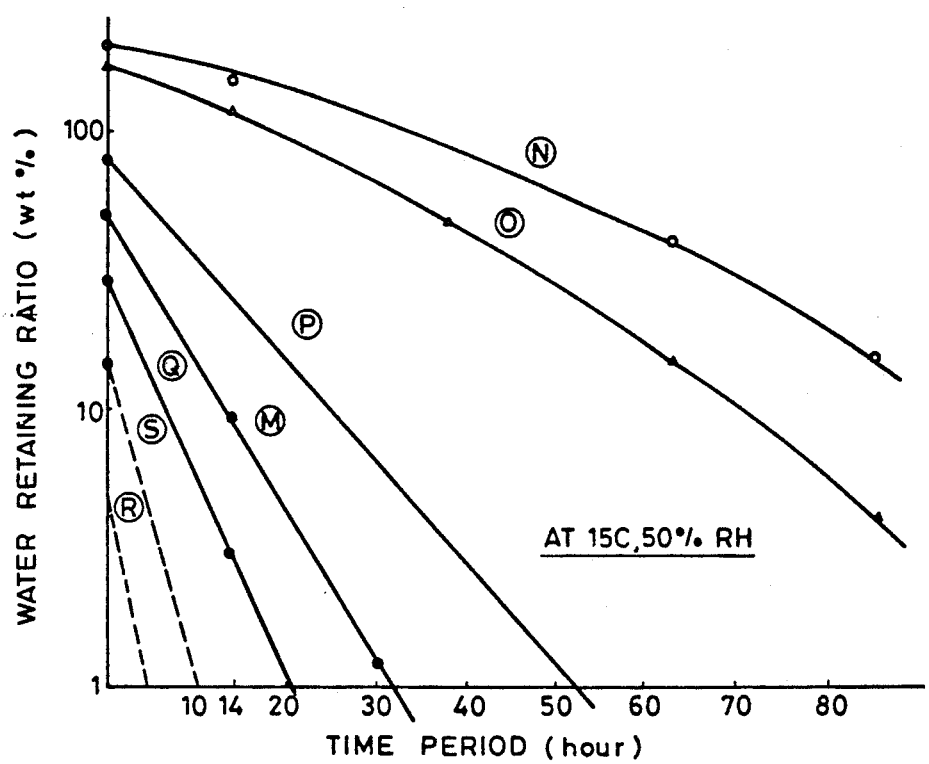
FIG. 7 is a graph showing the relationship between time period and water retaining ratio.

According to FIG. 7, initial moisture content ratio of the inorganic carriers (samples Q, R S) is lower than that of the porous glasses (samples M thru P), and water discharge speed from the inorganic carriers is higher than that from the porous glasses (see steep gradient lines Q, R and S in FIG. 7). Therefore, the inorganic carriers do not provide high water retaining percentages, and among the porous glass samples, samples N, O and P provided with low absolute specific gravity, and high moisture content ratio do provide high water retaining characteristic for a long duration of time.

Figure 8:
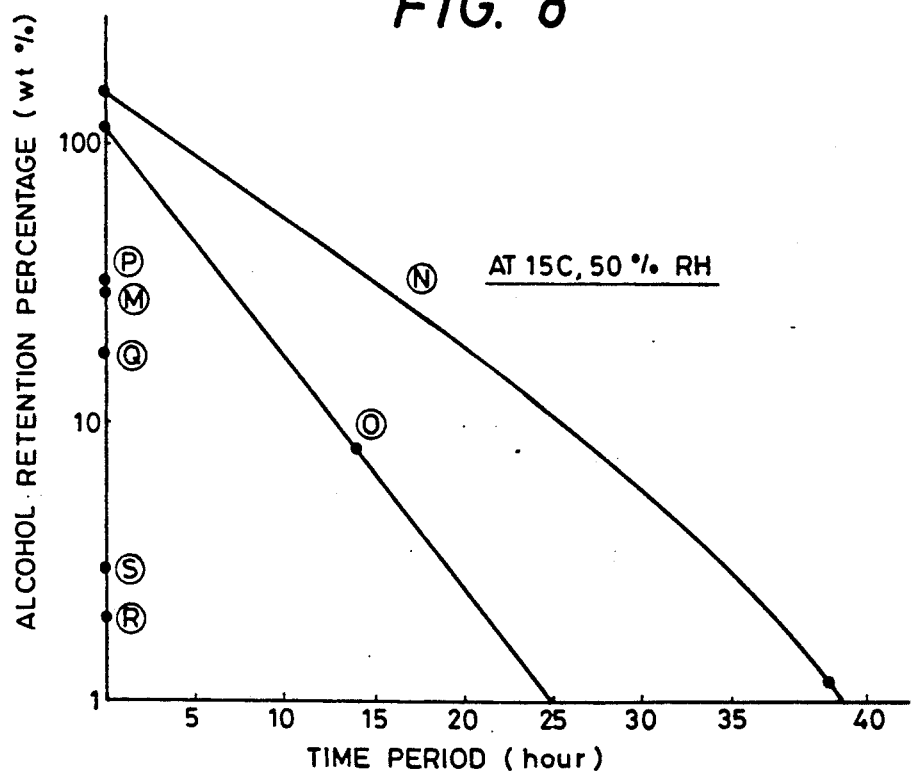
FIG. 8 is a graph showing the relationship between time period and alcohol retention percentage.

Another experiments were conducted to investigate retention percentages of samples M thru S shown in Table 8 by impregnating ethyl alcohol in the samples. Each of the samples had 5 grams in weight and weight of ethyle alcohol-impregnated samples was provisionally measured. Thereafter, the impregnated samples were placed in a beaker having an internal volume of 100 ml, under an ambient temperature of 15° C. and humidity of 50%. Then, weight of the samples was again measured in order to calculate retaining percentage (percent by weight) of the alcohol with respect to each of the samples. Test results are shown in FIG. 8. As is apparent from the graph shown in FIG. 8, only the samples N and O, which are porous glass samples, provided from 8 to 35% of alcohol retention percengates after 14 hours. On the other hand, with respect to the remaining samples, ethyl alcohol was immediately discharged therefrom.

Figure 9:
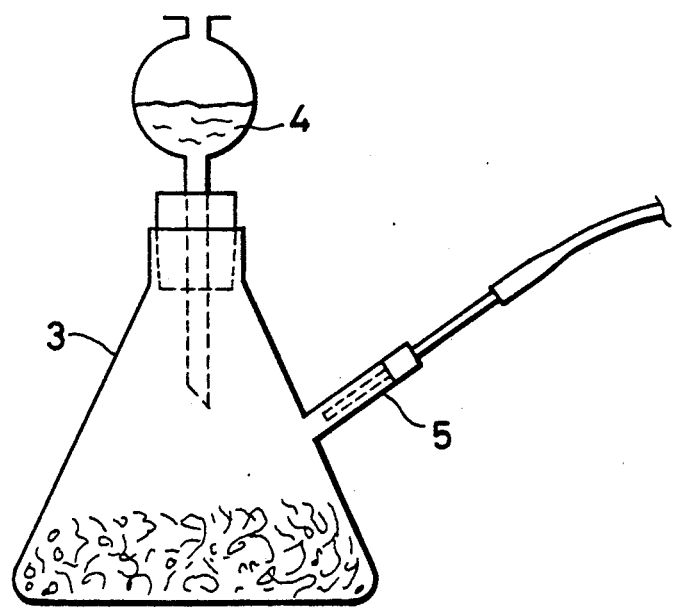
FIG. 9 is a schematic view showing fluid absorption treatment.

Through these experiments, the granular multi-cellular glass having prolonged service life is considered to provide the following physical properties:
apparent specific gravity: 0.05–0.70
moisture content ratio: 40.0–75.0%
median pore diameter: 1.0–50.0 μm In view of the above Examples, if the granular multi-cellular glass is provided with high moisture content ratio and high liquid retainability, such porous glass is available for various use because of its light weight characteristic as well. Further, the multi-cellular glass having the physical properties described above particularly provides prolonged service life in the field of aromatic technique, fertilizer, herbicide, hydroponics, microcarrier for yeast, enzyme and microorganism in biochemical reactor, fermentation accelerator in fermentation works, etc. For example, if such granular multi-cellular glass is used as a perfume carrier, the glass is placed in a side-arm flask 3, and perfume or other aromatic material 4 is dripped in the flask 3 as shown in FIG. 9. In this case, if vacuum source is connected to a side arm 5 for reducing pressure in the flask 3, liquid absorbing speed into the porous glass is increased.

The above described Examples concern increase in moisture content ratio and liquid retainability, and concern investigation of optimum physical properties of the granular multi-cellular glass. The Examples described below concern control of various physical properties. More specifically, in order to produce various porous glasses capable of being used in various kind of technologies, controls of various physical properties in the porous glasses are deemed to be necessary. Among the physical properties, grain diameter of the porous glass, compression strength, absolute specific gravity(drying state), and pore volume are easily controllable by suitably blending raw materials of the glass, and by controlling foaming and burning process. On the other hand, it would be rather difficult to control median pore diameter, moisture content ratio and specific gravity in water only by the above procedures.

The multi-cellular glass grain having low moisture content ratio and used as starting material may be known soda-lime glass, borosilicate glass, etc. In the following Examples, controlled are specific gravity and median pore diameter of the glass grain by controlling moisture content ratio thereof with dipping the glass in one of water and alkali solution. In this case, there is no specific requirement in respect of the kind of alkali solutions. For example, sodium carbonate solution and sodium hydroxide solution are available. By the control of the moisture content ratio of the multi-cellular glass grain, controlled is at least one of temperature of water or alkali solution, pH of the solution and dipping period. By this control, median pore diameter and specific gravity in water are easily and precisely controlled.

To be more specific, through extensive researches and developments, confirmed are mutual close relationship between the moisture content ratio and median pore diameter, between the ratio and specific gravity in water and between the ratio and apparent specific gravity in water, if the the starting multi-cellular glass grains are produced by the same conditions in terms of compositions of raw materials foaming and burning conditions. On a basis of these close relationships, median pore diameter and specific gravity in water of the glass grain are easily and precisely controllable. Further, obtained is the granular multi-cellular glass having constant grain diameter, constant compression strength, and constant pore volume, if the conditions of making the starting multi-cellular glass grains are the same in terms of glass compositions, blending, foaming and burning conditions, and more specifically, in terms of kinds of raw glass materials, pulverized glass particle diameter (average particle diameter and particle diameter deviation), amount and kind of foaming agent, burning temperature and burning period. In other words, (a) if the kinds of raw glass materials are the same, viscosity of the glass at the burning temperature is determined, (b) if the pulverized glass particle diameter is the same, equilibrium period of viscosity at burning temperature is determined, and, (c) if kind and amount of foaming agent is the same, foaming ratio (apparent specific gravity, pore volume and strength) is determined. Furthermore, burning temperature and burning period are also parameters for the control of the foaming ratio. Thus initially obtained multi-cellular glass grains (prior to dealkalization treatment) are processed in accordance with the present invention, so that targetting median pore diameter, specific gravity in water and apparent specific gravity in water of the final multi-cellular glass grain products are obtainable. Therefore, the multi-cellular glass grains produced by the method of this invention can be applied to various kinds of industries.

Through the following Examples 7 to 11, investigated is the controls of these physical properties of the granular multi-cellular glass (porous glass).

EXAMPLE 7

Prepared was soda-lime glass having compositions shown in Table 5, and the glass was pulverized so as to have average particle diameter of $X = 30$ μm, and particle diameter deviation of $\sigma = 50$ μm. 2.0 wt % of calcium carbonate ($CaCO_3$) was added to the glass particles as foaming agent, and the mixture was granulated. The granulated pellets were heated at a temperature of 800° C. for 200 seconds so that granular multi-cellular glasses having grain diameter of 3.0 mm were obtained. Of course, the granular glass provided low moisture content ratio. Physical properties of sample S-1 is shown in Table 9 (S-1 is the glass sample prior to dealkalization treatment).

Here, specific gravity in water and apparent specific gravity in water were measured by pycnometer method, and moisture content ratio was measured in the manner the same as that described in Example 1. Further, pore volume, specific surface area, median pore diameter (the diameter at which total pore volume, i.e., integral value, is divided into equally two volumes), average pore diameter, apparent specific gravity and porosity were measured by a pore sizer No. 9305, product of Micrometric Co., Ltd. in U.S.A., which utilizes mercury injecting method as also described in Example 4.

Various dealkalization treatments were made on the sample S-1. Conditions of the treatments are described at rightmost column in the Table 9 so as to increase moisture content ratio in the porous glass samples, to thereby provide samples S-2 through S-8. Physical properties of these samples were also measured in the manner the same as that of the sample S-1, and the properties are also shown in the Table 9.

According to Table 9, when the sample S-1 was dipped in hot water having temperature of 80° C. for 4 hours to obtain Sample S-2, moisture content ratio was 17.2%. However, if the sample S-1 was dipped for 5 hours in the hot water to obtain Sample S-3, moisture content ratio was increased to 22.5% (about 5% increase). Further, if the dipping period is increased further by 1 hour to obtain Sample S-4, the ratio became 30.4% (about 7% increase from sample S-3). Therefore, it is apparent that moisture content ratio is increased in accordance with the increase of the dipping period for dealkalization treatment, if the liquid temperature is the same.

With respect to the dealkalization treatment with using alkali solution such as 3% of $Na_2CO_3$ solution, if the sample S-1 was dipped for three hours to obtain Sample S-5, its moisture content ratio was 44.6%. However, if the sample was dipped further by 3 hours to obtain Sample S-7, its ratio was increased to 71.8%.

Furthermore, when the sample S-1 was dipped in 1.5% of NaOH solution having temperature of 80° C. for 3 hours to obtain Sample S-6, moisture content ratio was 60.4%. However, the ratio was increased to 76.3% when the sample S-6 was dipped further by 3 hours to obtain Sample S-8.

In view of the foregoing, alkali solution allows the multi-cellular glass to have greatly increased moisture content ratio rather than mere hot water. Further, when the samples were dipped in 3.0% of $Na_2CO_3$ solution and 1.5% of NaOH solution for 3 and 6 hours, greater amount of alkali components were eluted from the sample and such sample provided higher moisture content ratio when it was dipped in NaOH rather than dipped in $Na_2CO_3$ whose pH value is lower than that of NaOH.

Turning back to Example 2 and FIG. 4, it can be confirmed that moisture content ratio was increased if the sample was dipped in alkali solution rather than dipped in hot water, if the temperature of the liquids is the same. Further, higher temperature liquid provided higher moisture content ratio, if the kind of liquids is the same.

Figure 10:
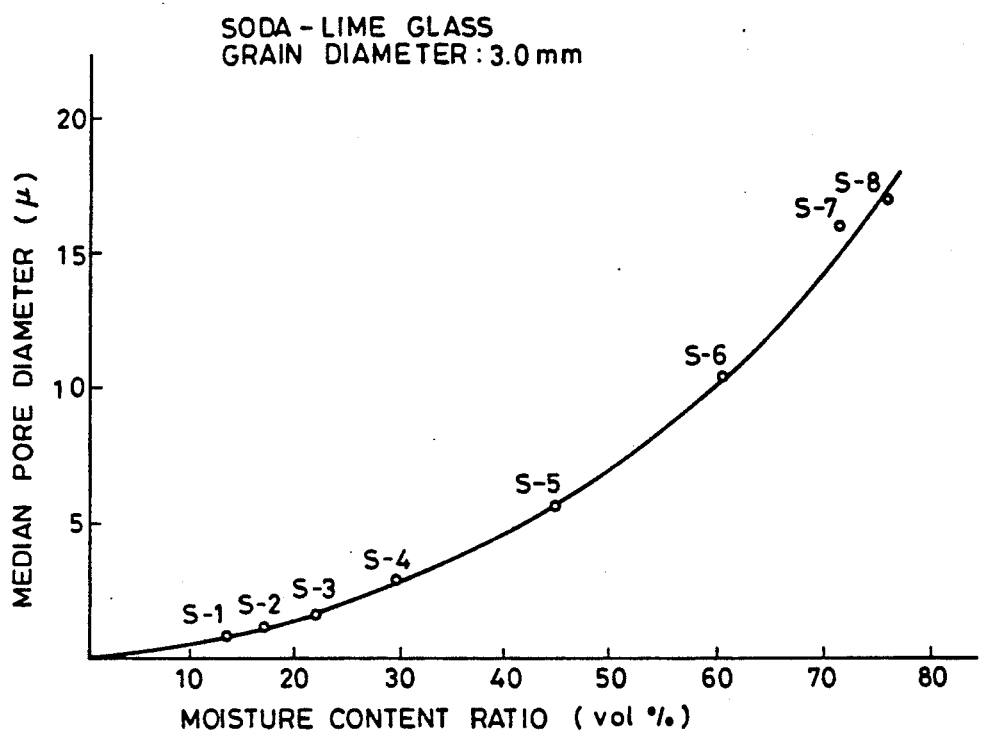
FIGS. 10, 12, 14, 16 and 20 are graphs showing the relationship between moisture content ratio and median pore diameter.

From the data shown in Table 9, plotted are the relationship between the moisture content ratio and the median pore diameter with respect to samples S-1 through S-8 as shown in FIG. 10. Also plotted were the relationship between the moisture content ratio and the specific gravity in water, and between the ratio and the apparent specific gravity in water with respect to these samples as shown in FIG. 11.

Figure 11:
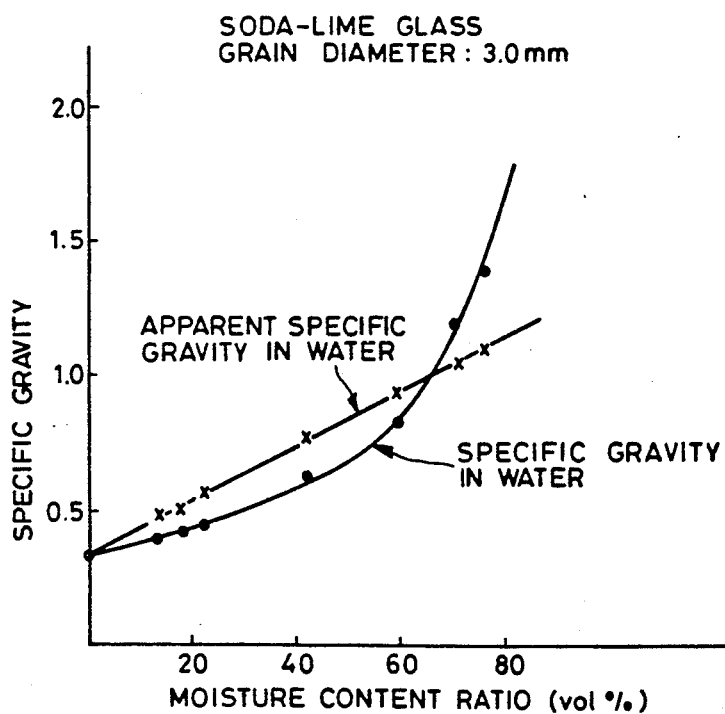
FIGS. 11, 13, 15, 17 and 21 are graphs showing the relationship between the moisture content ratio and specific gravity in water, and between the ratio and apparent specific gravity in water.

As is apparent from FIGS. 10 and 11, closed mutual relationship is acknowledgeable between the moisture content ratio and median pore diameter, between the ratio and the specific gravity in water, and between the ratio and the apparent specific gravity in water. Therefore, if moisture content ratio is determined by the dealkalization treatment, median pore diameter, specific gravity in water and apparent specific gravity in water are consequentially determinative.

Incidentally, as shown in FIG. 11, relationship between the moisture content ratio and the specific gravity in water would be different from the relationship between the ratio and apparent specific gravity in water. This difference is due to the fact that apparent specific gravity must be drawn into attention when the granular multi-cellular glass is dipped into the water and the water is agitated at relatively high speed. In this case, since the pore size of the glass is small, the porous glass containing water is considered to be separate from ambient water if the water agitation velocity is high. Therefore, the porous glass provides buoyancy corresponding to the apparent specific gravity in water. On the other hand, specific gravity in water must be drawn into attention when the porous glass is placed in water circulated by natural convection or placed in stationary water. In this case, the porous glass provides buoyancy corresponding to the specific gravity in water.

Therefore, when the granular multi-cellular glass or granular porous glass undergoes relatively low speed agitation as a microcarrier for immobilizing microbe which does not release gas in a fluidized bed type reactor for lactic fermentation, or when the porous glass is used as a microcarrier for incubation of zooblast in the fluidized bed, specific gravity in water of the microcarrier should be controlled to be substantially equal to the specific gravity of liquid culture medium on a basis of the relationship between the moisture content ratio and apparent specific gravity in water. On the other hand, when the carrier is subjected to high speed agitation, and when the carrier accompanies gas interchange, for example, if the carrier is used for immobilizing microorganism which releases gas, and the carrier is placed in a fluidized bed type reactor for alcoholic fermentation, attention should be drawn to both apparent specific gravity (dry state) and apparent specific gravity in water. With these procedure, accurate and fine controls to physical properties of the porous glass can be performed in accordance with various embodying styles.

EXAMPLE 8

Prepared was borosilicate glass having compositions shown in Table 5, and the glass was pulverized so as to provide average particle diameter $X=16.1$ $\mu$m, and particle diameter deviation of $\sigma=12.5$ $\mu$m. 2.5 wt % of calcium carbonate ($CaCO_3$) was added to the glass particles as foaming agent, and the mixture was granulated. The grains or pellets were then heated at temperature of 870° C. for 250 seconds, so that granular multi-cellular glasses (porous glass grain) having grain diameter of 3.0 mm were obtained. Physical properties of the samples $B_1$-1 are shown in Table 10.

Next, various dealkalization treatments were performed to the sample $B_1$-1 in accordance with conditions described at rightmost column in Table 10, so that samples $B_1$-2 through $B_1$-8 were obtained, and physical properties of these samples are also shown in Table 10. Incidentally, in this Example 8, relationships between the moisture content ratio and dipping period for dealkalization treatment, between the ratio and the temperature of the dipping liquid, and between the ratio and the pH of the liquid were the same as the relationships as those described in Example 2.

Figure 12:
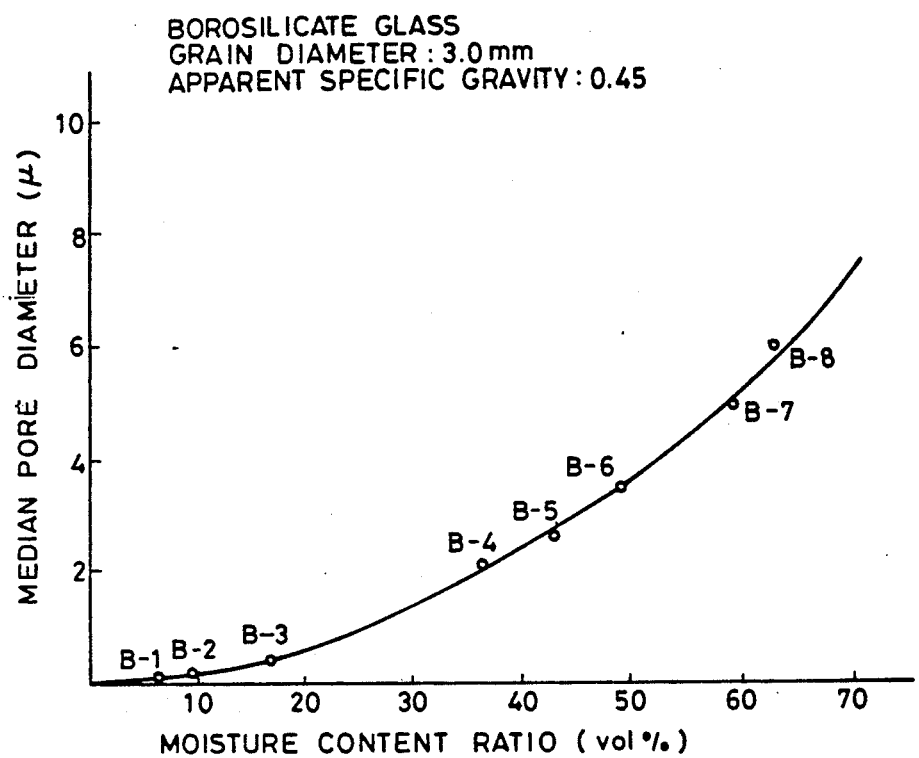
Figure 13:
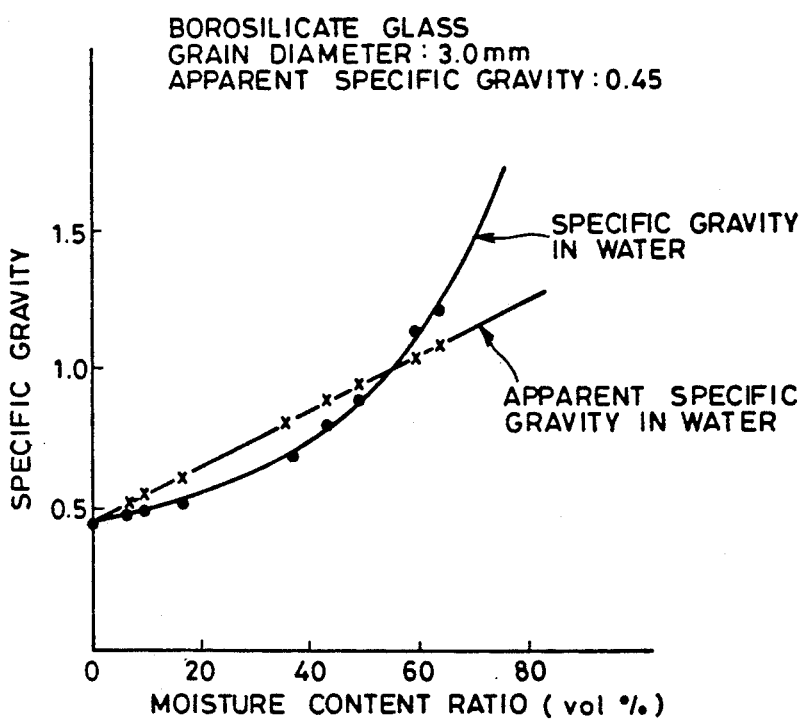

From the data shown in Table 10, plotted are the relationship between the moisture content ratio and the median pore diameter as shown in FIG. 12, and between the ratio and the specific gravity in water and between the ratio and the apparent specific gravity in water as shown in FIG. 13 with respect to these samples.

In view of FIGS. 12 and 13, similar to the Example 7, close mutual relationships can be found between the moisture content ratio and the median pore diameter, and between the ratio and specific and apparent specific gravity in water.

EXAMPLE 9

Prepared was borosilicate glass having the compositions the same as that of Example 8 and shown in Table 5, and the glass was pulverized so as to provide average particle diameter of $X=21.2$ $\mu$m, and particle diameter deviation of $\sigma=20.0$ $\mu$m. 1.5 wt % of calcium carbonate ($CaCO_3$) and 1.5 wt % of sodium nitrate ($NaNO_3$) were added to the glass particles as foaming agent, and the mixture was granulated. The grains or pellets were then burned at temperature of 890° C. for 200 seconds, so that granular multi-cellular glasses (porous glass grains) having grain diameter of 2.0 mm were obtained as samples $B_2$-1. Physical properties of the samples are shown in Table 11.

Next, various dealkalization treatments were performed to the samples $B_2$-1 in accordance with conditioned described at rightmost column in Table 11, so that samples $B_2$-2 through $B_2$-8 were obtained, and physical properties of these samples are also shown in Table 11. Incidentally, in this Example 9, relationships between the moisture content ratio and dipping period for dealkalization treatment, between the ratio and the temperature of the dipping liquid, and between the ratio and the pH of the liquid were substantially the same as the relationships as those described in Example 2 and Example 8.

Figure 14:
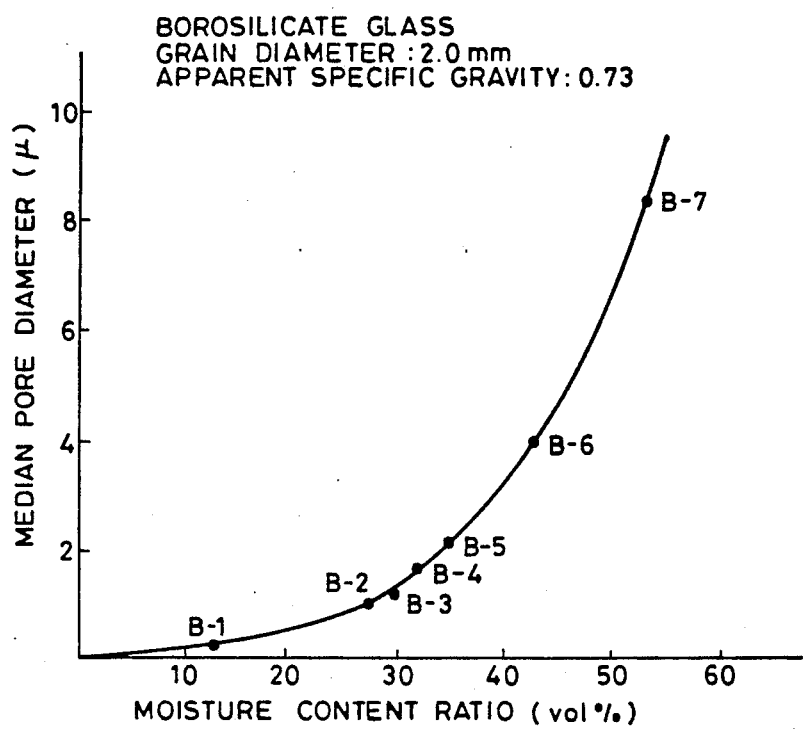

From the data shown in Table 11, plotted are the relationship between the moisture content ratio and the median pore diameter as shown in FIG. 14. Also plotted are the relationship between the ratio and the specific gravity in water and between the apparent specific gravity in water as shown in FIG. 15 with respect to these samples.

Comparing Examples 8 with Example 9, and comparing FIG. 12 and FIG. 14, when the grain diameter of the porous glass becomes small(from 3 mm to 2 mm), increased is the degree of increase in median pore diameter in accordance with the increase of the moisture content ratio. Further, comparing FIGS. 15 with FIG. 13, difference between the specific and apparent specific gravities in water becomes smaller in Example 9 than that in Example 8.

Figure 15:
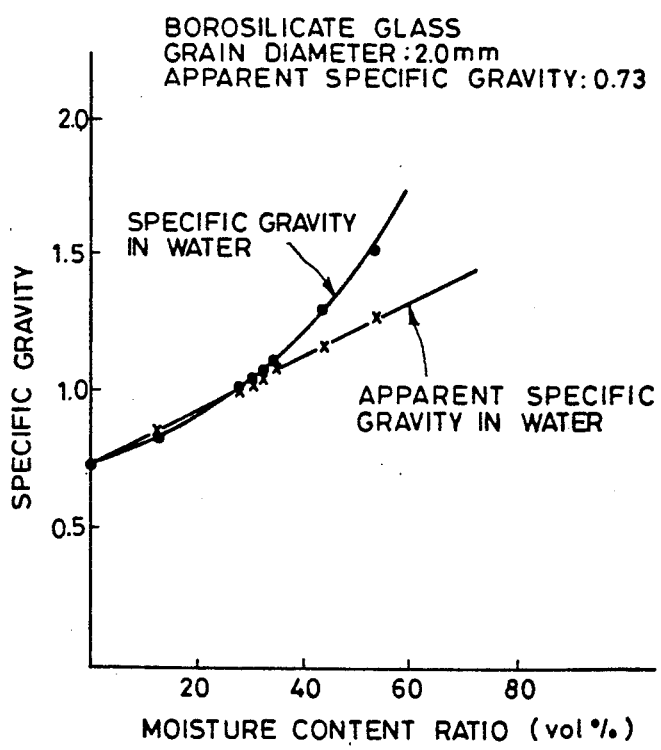

According to FIGS. 14 and 15, similar to the Examples 7 and 8, close mutual relationships are also acknowledged between the moisture content ratio and median pore diameter, between the ratio and specific gravity in water, and between the ratio and apparent specific gravity in water.

EXAMPLE 10

Prepared was soda-lime glass having compositions the same as that of Example 7 and shown in Table 5, and the glass was pulverized so as to provide avarage particle diameter $X=19.9$ μm, and particle diameter deviation of $\sigma=15.6$ μm. 2.5 wt % of sodium nitrate ($NaNO_3$) was added to the glass particles as foaming agent, and the mixture was granulated. The grains or pellets were then burned at temperature of 810° C. for 150 seconds, so that obtained were granular multi-cellular glasses (porous glass grains) having grain diameter ranging from 350 to 500 μm which is available for a microcarrier. Physical properties of the glasses are shown in Table 12 as a sample M-1.

Next, various dealkalization treatments were performed to the samples M-1 in accordance with conditions described at rightmost column in Table 11, so that samples M-2 thorugh M-10 were obtained, and physical properties of these sampels are also shown in Table 12. Incidentally, physical properties were measured by the procedure the same as that of Example 7.

Figure 16:
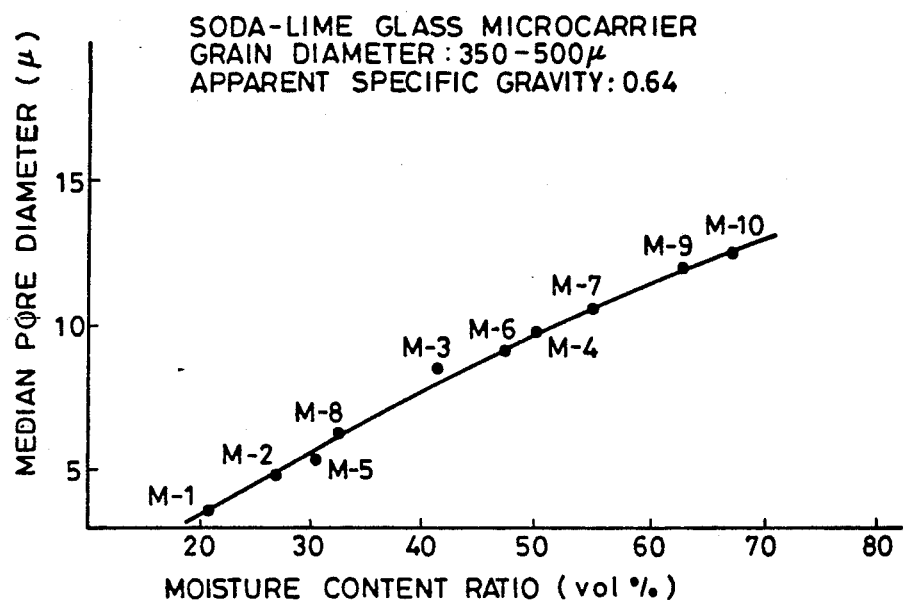
Figure 17:
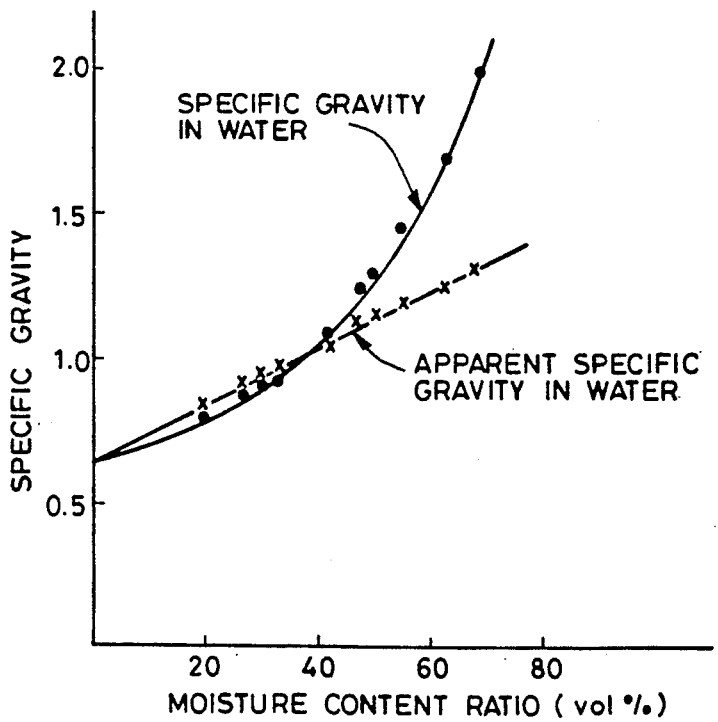

From the data shown in Table 12, plotted are the relationship between the moisture content ratio and the median pore diameter as shown in FIG. 16, and between the ratio and the specific gravity in water and between the ratio and the apparent specific gravity in water as shown in FIG. 17 with respect to these samples.

In this Example 10, grain diameter of the sample was extremely small, and linear relationship is acknowledged between the moisture content ratio and the median pore diameter. Further, similar to Examples 7 through 9, close mutual relationships can be found between the moisture content ratio and the median pore diameter, and between the ratio and specific and apparent specific gravities in water as is understood from FIG. 17.

Example 7 used the soda-lime glass having the composition the same as that used in Example 10, and Example 8 used the borosilicate glass having the composition the same as that used in Example 9. Between Examples 7 and 10, and between the Examples 8 and 9, it is understood that various combinations could be obtained in the relationships among the median pore diameter, specific gravity in water and apparent specific gravity in water relative to the moisture content ratio by changing or controlling successive production steps starting from raw material blending or mixing step and terminating by the foaming and burning step.

Figure 18:
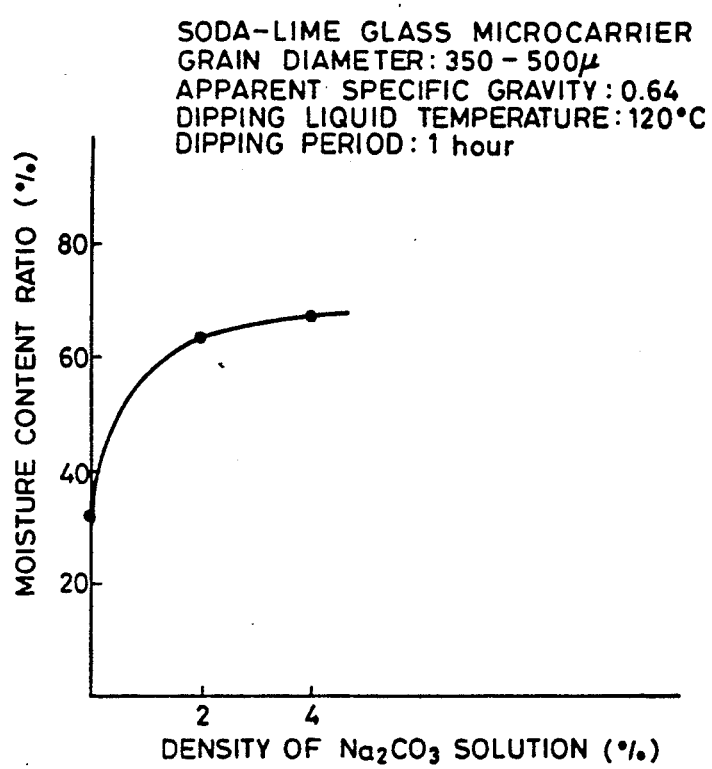
FIG. 18 is a graph showing the relationship between the solution density and moisture content ratio.

FIG. 18 shows the relationship between density of sodium carbonate for the dealkalization treatment and moisture content ratio with respect to the Samples M-4, M-9 and M-10 shown in Table 12. These samples provided grain diameters ranging from 350 to 500 μm as described above, and were subjected to dealkalization treatment by dipping into sodium carbonate solutions each having density different from one another at temperature of 120° C. for 1 hour. (see conditions described at rightmost column of Samples M-4, M-9 and M-10, in which the sample M-4 is considered to be dipped in sodium carbonate solution having density of zero percent.) According to FIG. 18, the increase in moisture content ratio is noticeable by the increase in density of $Na_2CO_3$ solution.

Figure 19:
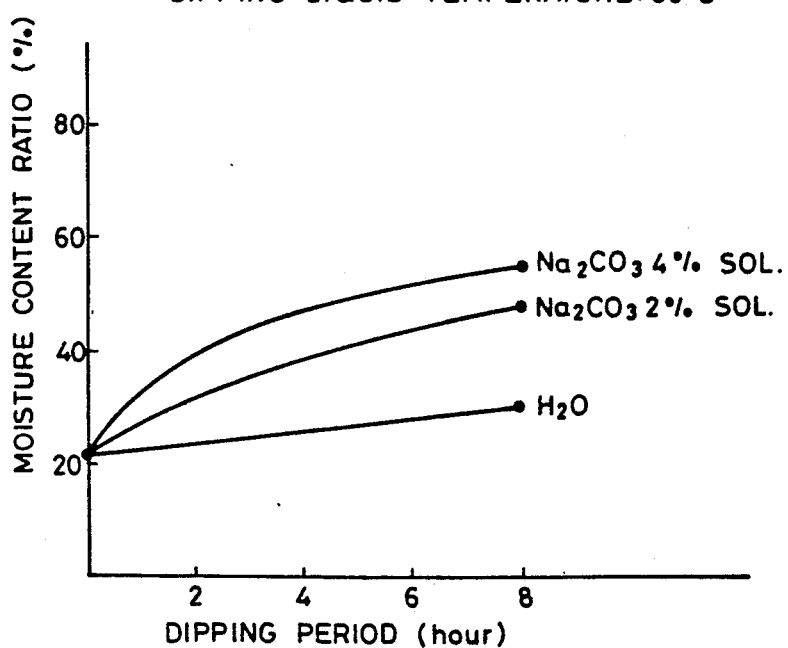
FIG. 19 is a graph showing the relationship between the dipping period and the moisture content ratio; and, FIG. 22 is a graph showing the relationship between specific gravity in water and the median pore diameter.

FIG. 19 shows the relationship between dipping period for dealkalization treatment and the moisture content ratio with respect to samples M-1 to M-3, M-5 to M-6, and M-7 to M-8 in which densities of sodium carbonate are parameters. In FIG. 19, grain diameter was ranging from 350 to 500 μm as described above, and dipping solution temperature was 80° C. According to FIG. 19, moisture content ratio was gradually increased when the density of alkali solution becomes high and dipping period is prolonged. If the sample was dipped in hot water, the moisture content ratio was gradually and linearly increased with the increase of the dipping period.

EXAMPLE 11

Prepared was soda-lime glass having compositions the same as that of Example 7 and shown in Table 5, and the glass was pulverized so as to provide average particle diameter $X=16.1$ μm, and particle diameter deviation of $\sigma=12.5$ μm. 2.0 wt % of calcium carbonate was added to the glass particles as foaming agent, and the mixture was granulated. The grains or pellets were then heated at temperature of 800° C. for 200 seconds, so that granular multi-cellular glasses (porous glass grains) having grain diameter of 3.0 mm were obtained as Samples $S_2$-0. Physical properties of the samples $S_2$-0 are shown in Table 13.

Next, various dealkalization treatments were performed to the samples $S_2$-0 in accordance with conditions described at rightmost column in Table 13, so that samples $S_2$-A, $S_2$-B and $S_2$-C were obtained. Three kinds of solutions for the dealkalization treatment were prepared, i.e., 5% of $Na_2CO_3$ solution, 5% of HCl solution, and hot water. Each of the solutions had temperature of 80° C. and these samples were dipped for 12 hours. Physical properties of these samples are also shown in Table 13.

Figure 20:
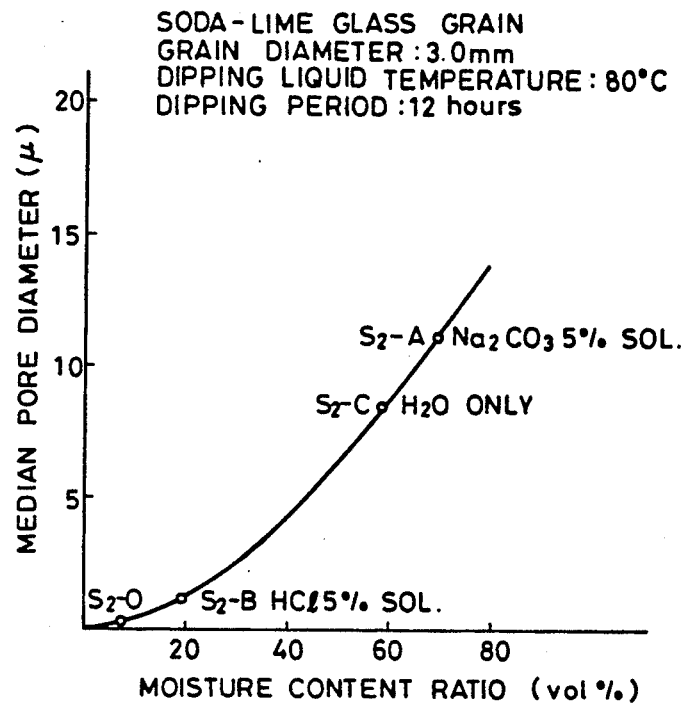
Figure 21:
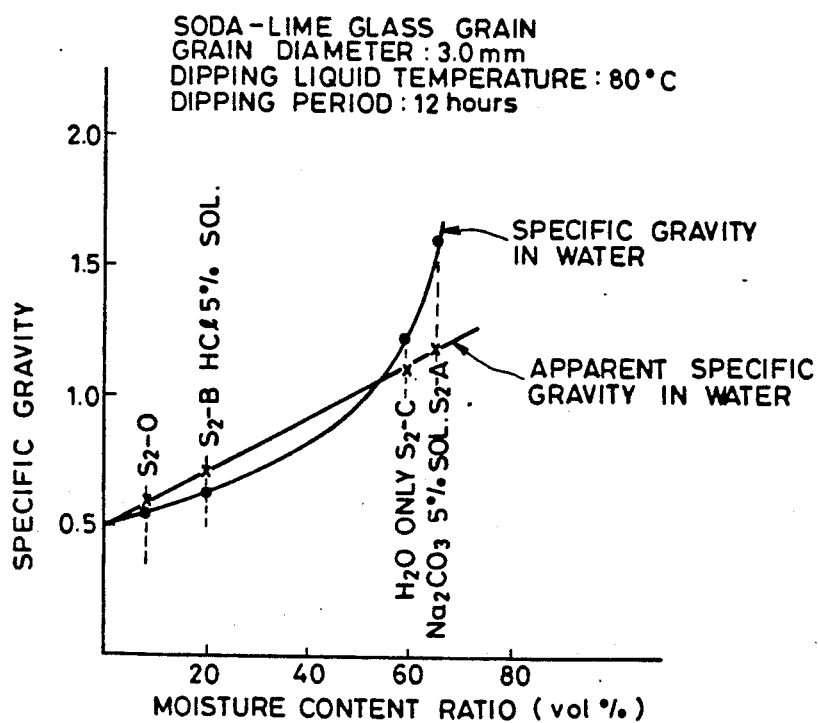

From the data shown in Table 13, plotted are the relationship between the moisture content ratio and the median pore diameter as shown in FIG. 20, and the relationships between the ratio and specific and apparent specific gravities in water as shown in FIG. 21.

As is understood from FIG. 20, employment of hot water or 5% of $Na_2CO_3$ solution provided higher dealkalization effect than that of 5% of HCl. Further, similar to the Examples 7-10, close relationships are acknowledgeable between the moisture content ratio and median pore diameter, and between the ratio and specific and apparent specific gravities in water.

Figure 22:
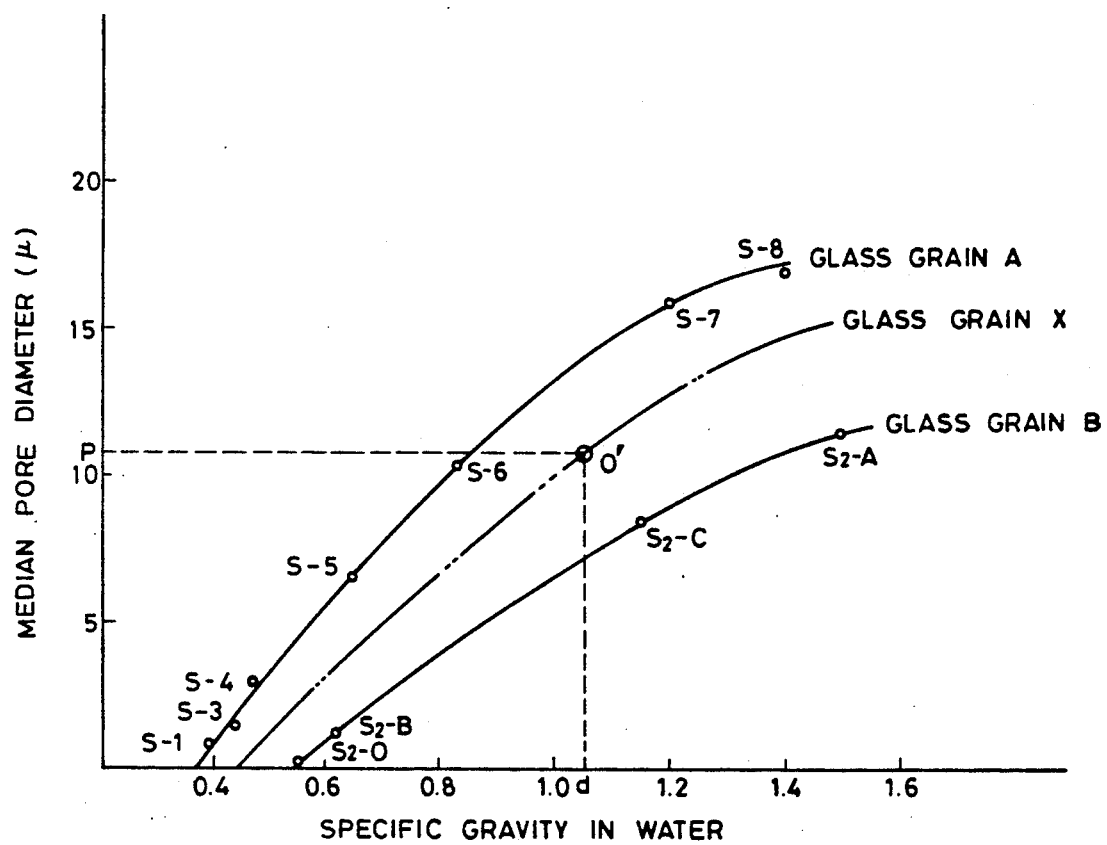

Comparing Example 7 with Example 11, only the particle diameter in the initial pulverizing steps are different from each other prior to dealkalization treatment. FIG. 22 shows the relationship between the specific gravity in water and median pore diameter, and in the curves of the graph, particle diameters in pulverizing step are given as parameters. As is apparent from FIG. 22, two curves are directed substantially in parallel with each other. Further, median pore diameter with respect to the samples having small particle diameter (Example 11) in pulverizing step was generally lower than that to the samples having large particle diameter (Example 7) in pulverizing step. Furthermore, specific gravity in water is increased in case of the emplyment of particles having small diameter rather than that having large diameter. In other words, the sample formed of relatively large diameter particles in pulverizing step provides relatively large median pore diameter and low specific gravity in water in comparison with the sample formed of relatively small diameter particles in pulverizing step.

Therefore, if optimum mean pore diameter (P) and specific gravity in water (d) are required for a granular multi-cellular glass carrier, the graph having the relationship similar to FIG. 22 is drawn with respect to the granular multi-cellular glasses produced by the steps and conditions the same with each other except particle diameter in pulverizing step, and then the desired pore diameter P and specific gravity in water d is plotted as a point 0′. Next, an imaginary curve (as shown by a two-dotted chain line in FIG. 22) is drawn which passes through the point 0′ in parallel with the already fixed curves (for exmaple, the curves A and B). Thereafter, prepared was the glass particles which corresponds to the imaginary curve, and the particles was mixed with the foaming agent, and granulated and burned at the conditions the same as those for making samples A and B in FIG. 22. Then, the obtained glass grain is subjected to dealkalization treatment so as to provide the optimum moisture content ratio which ratio corresponds to the optimum specific gravity in water and optimum median pore diameter. Accordingly desired porous glass grain having the desired physical properties is produced.

The same is true with respect to the apparent specific gravity in water in addition to the specific garvity in water.

In view of the foregoing Examples, the present invention increases moisture content ratio by the dealkalization treatment in which granular multi-cellular glass having initially low moisture content ratio are dipped into water or alkali solution. Further, in Examples 7 through 11, controlled is the various physical properties such as median pore diameter, specific gravity in water and apparent specific gravity in water those being closely related to the moisture content ratio. Such physical properties are easily and accurately controllable, so that multi-cellular glass grains according to the present invention are available for various kind of use.

The multi-cellular glass or porous glass according to the present invention is particularly available as a microbial hold-back carrier, i.e., a carrier for immobilizing microbe. The porous glass is therefore, capable of performing immobilization of yeast, and is applicable for a method of producing liquor employing yeast immobilized in the microcarrier. The porous glass provided with not less than 50% of moisture content ratio is usable as the microcarrier. Next, the microbial hold-back carrier will be described in detail.

As described above, the highly porous glass according to the present invention is provided with a great number of blisters or cells at its surface layer and its interior. And almost all the blisters or cells are considered to be open cells in which neighbouring cells are in fluid communication with each other through the micropores or pinholes, and high moisture content ratio is provided such as not less than 50%. In the cell walls, a plurality of pin holes are formed, which structure is deemed to further enhance the moisture content ratio.

Median pore diameter and pore volume or other physical properties of the porous glass be changed in accordance with the variation of the microbe to be immobilized therein. Suitable physical properties for the immobilization of yeast will be described later. Further, if Zymomonas bacteria is to be immobilized, the microcarrier should preferrably provide median pore diameter of 0.4 to 10 $\mu$m, and pore volume of 0.5 to 2.0 ml/g.

Various shapes are applicable as the microcarrier. However, granular shape is typical configuration. In this case, grain diameter implies maximum diameter of the grain in the description below.

Various kinds of microbe can be immobilized to the microcarrier according to the present invention. Specifically, available are yeasts, lactobacilli, Zymomonas bacteria, etc. Among these, yeast are the typical microbe for producing liquor or alcoholic drinks. However, other kinds of microbe are also immobilized in the microcarrier in the manner the same as that of yeast.

Immobilized microbes in the present invention generally provide high immobilization ratio and low degree of desorption or release from the microcarrier. In case of the yeast, not less than $10^6$ cells/cm$^2$ of yeasts per unit surface area can be immobilized, and only not more than 1% of detachment from the carrier is obtainable (measuring method will be described later).

The immobilized microbe according to the present invention can be employed in various use. For example, if immobilized yeast is used, liquor can be produced by using various types of sugars as substrate. Further, if immobilized Zymomonas bacteria is used, ethanol can be produced by using sugar, particularly blackstrap molasses, as substrate.

Fermentation starting liquid contains substrate of yeast employed. Ordinarily, the liquid contains solution or dispersive liquid which contains sugar as substrate, and specifically, wort in case of the production of beer and whisky, fruit juice in case of the production of wine, and unrefined sake (a portion excluding yeast) in case of the production of Japanese sake and Japanese shochu (low class distilled spirits).

Further, various kinds of yeasts can be applied to the highly porous glass grains according to the present invention. For example, Saccharomyces cerevisiae, or other ordinary kind of yeast for liquor production are available. For the immobilization, the highly porous glass grain according to the present invention is used as the microcarrier. In this case, the porous glass should provide median pore diameter of 1.0 to 50 $\mu$m, preferably 20 to 40 $\mu$m, pore volume of 1.0 to 5.0 ml/g, preferably 2.0 to 3.0 ml/g, moisture content ratio of 50 to 90%, preferably 50 to 85%, and bulk specific gravity of 0.1 to 0.5, preferably 0.2 to 0.35. If one of the median pore diameter and pore volume is excessively smaller than the above described ranges or if both diameter and volume are smaller than the above ranges, immobilization amount of the yeast becomes lowered. On the other hand, if median pore diameter is excessively larger than the above range, immobilized yeast is easily detached from the carrier. Further, if one of the median pore diameter and pore volume is excessively larger than the above-described ranges or if both diameter and volume are larger than the ranges, strength and durability of the immobilized yeasts are degraded. In this connection, optimum physical properties of the glass should be selected within the above-described ranges in conjunction with the purpose and kinds of microbes or yeasts.

As described above, moisture content ratio and bulk specific gravity are determinative by the median pore diameter and pore volume. Size and configuration of the porous glass is changeable in accordance with the kinds of fermentation reactor, etc. Various kinds of configurations are available such as grain shape, plate shape, rod shape having rectangular or circular cross-section, honeycomb shape or other polygonal shape. However, in view of reaction efficiency and handling performance, preferable is grain shape having diameter of 0.5 to 15 mm, preferably 1.5 to 15 mm, and most preferably, 2 to 6 mm. If the grain is not completely spherical shape, the diameter referred herein is the maximum diameter.

The multi-cellular glass or porous glass is formed of silica glass, soda-lime glass, aluminoborosilicate glass, borosilicate glass, aluminosilicate glass or lead glass. However, in view of economical standpoint, soda-lime glass is preferably selected. Method of producing highly porous glass is described in the foregoing Examples. For example, granular multi-cellular glass having moisture content ratio of 5 to 20% produced by the conventional method is dipped in hot water or alkali solution so as to eluate soluble alkalic component and silica from the glass, so that micropores or pinholes are formed at a surface layer and walls of the closed cells in the glass. Alternatively, highly porous glass is also produced by mixing glass powders with 5 to 10% of foaming agent and metal oxide having high melting point such as alumina, silica and zirconia, burning the mixture and then immediately cooling the burned mixture as disclosed in Japanese patent publication No. 55-340 and Japanese Patent Application Pubication (kokai) No. 61-6141.

Attachment or immobilization of the yeast to the highly porous glass is conducted by contacting the glass with the yeast suspension for a predetermined period of time. Any kinds of dispersive medium is available for suspension of the yeast unless the medium causes halmful effect in view of food health sanitation and unless the medium affects activation of yeast. Generally, brewer's raw material liquid, fermented liquid, water and mixture thereof are applicable. Population of yeast in the yeast suspension is properly controlled so as to obtain predetermined population of the immobilized yeasts. Generally, the population of yeast in the yeast suspension is set higher than that of the immobilized yeasts. In case the dispersant contains fermentation starting liquid, yeasts can be attached to the porous glass with culturing and multiplicating the yeast in the dispersive medium. In this case, initial population of yeast in yeast suspension can be set at low level. Contacting period between the porous glass and the yeast suspension is about one to two days. Even if the period is prolonged to more than two days, population of immobilized yeasts is not so increased, since the population is dependent primarily on physical properties of the porous glass such as pore volume, median pore diameter, etc. However, if the immobilization of yeast is performed with cultivating and multiplicating the yeast in the fermentation starting liquid, multiplication period should also have to be considered. Various manners of contact between the porous glass and the yeast suspension can be conceivable as long as sufficient contact therebetween is achievable. For example, if the yeast is to be attached to the porous glass grain, the glass grain is dipped in the suspension and is left as it is, or is agitated. Alternatively, porous glass grains are filled in a cylindrical column, and yeast suspension is circulated through the column. Detailed method for immobilization of yeast will be described later.

Turning to the production of liquor or alcoholic beverages, the fermentation starting liquid is subjected to fermentation with contacting the liquid with the immobilized yeast as described above. For the fermentation, various types of processes can be conceivable. For example, fermentation starting liquid is supplied in batch system to a reactor in which immobilized yeast in the porous glass grain is used as a fixed bed, non-fixed bed or fluidized-bed. Alternatively, the liquid is continuously supplied in a single circulation or plurality of circulations into the reactor. Details of these bio-reactor processes are disclosed in "Enzyme Engineering" published by Tokyo Chemistry Coterie co-authored by Saburo Fukui, Ichiro Chihata, and Shuichi Suzuki, or "Biotech. and Bioeng. 23 1813-25 (1981) co-authored by D. Williams, and D. M. Munnecke. Filling up ratio of the immobilized yeast carrying grains into the reactor is changeable. However, in order to make use of the advantages attendtant to yeast immobilized in the highly porous glass grain, high yeast population or concentration such as not less than 0.4 w/v% is preferable in case of rapid production of liquor. In the units, "w" is weight (gram) of yeast contained in the porous glasses in the reactors but the yeast is converted into drying condition, "v" is volume(ml) of fermentation starting liquid in case of batch system or is an internal volume of reactor(ml) which accomodates the glass grains containing immobilized yeast in case of continuous fermented system. Further, fermentation or other conditions according to the present invention would be the same as that of the conventional conditions unless otherwise provided. Resultant fermentation liquid may be liquor. However, the liquor is preferably further subjected to aging or maturation for obtaining final product. Detailed Examples will be described below.

EXAMPLE 12

Part 1

Production of multi-cellular glass grain

Soda-lime glass having compositions shown in Table 5 was prepared, and the glass was subjected to levigation or elutriation for 24 hours. Obtained glass particles had average particle diameter of 30 $\mu$m and particle diameter deviation of 50 $\mu$m. The glass particles was mixed with 2% of $CaCO_3$ as foaming agent, and the mixture was granulated. The granulated pellets were burned at temperature of 820° to 850° C. for 100 to 150 seconds. Thus obtained multi-cellular glass grain was dipped in hot water having temperature of 70° C. for 4 days, so that highly porous glass grains were obtained. Physical properties of the glass grains (sample Nos. 1 thourgh 8) are shown in Table 14. In Table 14, pore volume and pore surface area were measured by mercury injecting method by means of Pore sizer 9305 product of Micrometrics Co.,Ltd., U.S. company.

Part 2

Immobilization of yeast

Beer yeast (*Saccharomyces cerevisiae*) was suspended in wort whose sugar percentage was controlled to 11° P., so that the yeast concentration or population degree became $6.0 \times 10^8$ cells/ml. In the yeast suspension, about 15% of porous glass grain samples were dipped (this percentage was calculated by dividing volume of porous glass grain by wort volume). Then batch type agitation was carried out at agitation velocity of 200 r.p.m. and at temperature of 8° C. for about 48 hours, so that yeast was immobilized or attached to the porous glass grain samples. Numbers of immobilized yeast and their release percentages from the samples are shown in Table 15. Definitions of leftmost items in Table 15 are as follows;

*1, *2, and *3

*1—yeast cell numbers in unit volume: x/y
*2—yeast cell numbers in unit surface area: x/z
*3—yeast cell numbers in unit weight: x/w in which,
x(cells): yeast cell numbers immobilized in a single porous glass grain;
y(ml): volume of porous glass grain sample employed as microcarrier (the volume includes the pore volume into which no water is absorbed by 1 minute dipping in water at normal atmospheric pressure)
z(cm$^2$): surface area of the porous glass sample used as microcarrier. (assuming that the employed sample is not porous member but a smooth outer surface member, e.g., provided that the glass grain has a radius "r cm", z=$4\pi r^2$cm$^2$.)
w(g): weight of porous glass grain employed as the microcarrier.

[*4]

Yeast release or desorption percentage from the porous glass samples are measured by the following procedures:

A cylindrical cage having inner diameter of 33 mm and depth of 95 mm and provided with quadrate mesh having each side length of 1.5 mm was disposed within and coaxial with a beaker having internal volume of 500 ml. In this disposition, 2 cm distance was provided bewteen the bottom of the cage and the beaker bottom. 15 numbers of porous glass samples in which yeast was immobilized were put into the cage, and 400 ml of water was poured in the beaker and the water was agitated at agitation speed of 700 r.p.m. for 48 hours by using a stirrer bar having an axial length of 5 cm. Thus, yeast release percentage Z(%) is represented by the following formula;

$$Z = (1 - Y/X) \times 100$$

in which,
X: numbers of yeast cells immobilized in the porous glass prior to agitation(cells/single carrier);
Y: numbers of yeast cells immobilized in the porous glass after agitation (cells/single carrier).

Incidentally, this procedure is only available for the spherical porous glass having diameter ranging from 1.5 to 15 mm, and such glass is used as a microcarrier for immobilization of yeast.

Part 3

Production of liquor

Immobilized yeast obtained in Part 2 above was used to produce beer. 200 ml of wort having controlled sugar percentage of 11.0° P was flowed in a measuring cylinder having an internal volume of 250 ml, and 30 ml of immobilized yeast carrying sample 2 shown in Table 15 was added in the wort. The mixture was maintained as it is at temperature of 8° C. for 50 hours, and then batch type beer brewage was carried out. Characteristics of resultant beer are shown in Table 16.

Part 4

Production of liquor

Immobilized yeast carrying samples 3 shown in Table 15 were filled in a cylindrical column having inner diameter of 3.5 cm and depth of 30 cm. Then wort having controlled sugar percentage of 11.0° P and temperature of 8° C. was poured through the column by every 10 ml per hour, so that continuous beer brewage was carried out. In this brewage, immobilized yeast carrying porous glass sample provided sufficient strength and durability, and beer having characteristics shown in Table 17 can be produced in stabilized fashion for more than 10 days.

EXAMPLE 13

Part 1

Production of multi-cellular glass grain

Prepared was borosilicate glass having composition shown in Table 5. The glass was pulverized so as to provide average particle diameter of 22.0 μm. 3% of CaCO$_3$ was added to the glass particles as foaming agent, and the mixture was granulated so as to provide average pellets diameter of 2.00 to 2.38 mm. The pellets were heated at temperature of 870° C. for 200 seconds, so that multi-cellular glass grains were produced. Thus obtained glass grains were subjected to dealkalization treatment in the manner the same as that described in Example 1. That is, the glass grains were dipped in 3% of NaOH solution (120° C.) in an autoclave having temperature of 120° C. for 4 hours. As a result, highly porous glass Samples 9 and 10 having physical properties shown in Table 18 were obtained. In Table 18 methods of measuring star-marked properties were the same as those in Table 14 (Example 13).

Part 2

Immobilization of bacteria in the Samples 9 and 10

*Zymomonas mobilis* (ATCC 10988) was suspended in liquid culture medium having pH of 6 to 7 and which contains 1.0 w/v% of yeast extract and 10.0 w/v% of sucros so as to provide concentration of *Zymomonas mobilis* of $1.8 \times 10^6$ cells/ml. In this suspension, about 5% (w/v) of Samples 9 and 10 were dipped and were stationarily cultured for 24 hours at temperature of 30° C. so as to immobilize *Zymomonas mobilis* into the Samples. Cell numbers of immobilized *Zymomonas mobilis* are shown in Table 19.

According to the foregoing Examples and particularly to Examples 12 and 13, highly porous glass provides high strength and durability and is capable of being used as a microcarrier. The highly porous glass is formed with a plurality of pinholes or micropores having diameter of 0.3 to 2000 μm at its interior portion as well as its outer surface. Therefore, microorganism such as yeasts can be multiplicated and fixed even at the internal portion of the glass in addtion to the outer surface portion thereof. Accordingly, higly concentrated attachement of the microbe to the porous glass carrier is obtainable regardless of the employment of cross-linking agent. Further, microbe cell numbers can be controlled in variety of ranges by suitably selecting median pore diameter and pore volume of the porous glass.

If the higly porous glass or multi-cellular glass according to the present invention is used in the field of brewage, the following advantages are attainable:

(a) Continuous liquor production for long period of time and batch system liquor production repeatedly using the same yeast carrying carrier can be conducted, since the immobilized yeast carrying glass provides high strength and durability with eliminating its swelling, shrinkage and deformation. Further, since the carrier is formed of glass, the carrier provides stabilized performance against various service conditions such that the carrier is sustainable against wide pH ranges and various ions during liquor production. Furthermore, even if a packed-bed type reactor is used for the liquor production, highly efficient operation is performed with minimized pressure loss in the reactor, since the immobilized yeast carrying carrier has high compression strength and its specific gravity is controllable in a wide range.

(b) The carrier provides excellent food health sanitation, since the carrier is formed of a glass material and since cross-linking reagent is not required for the immobilization of yeast in contrast to the conventional porous ceramic carrier. Further, higly concentrated yeast can be immobilized, so that rapid liquor production is attainable because of high rate fermentation.

(c) Since the microcarrier is formed of glass material, it is stable against heat and medicine. Accordingly, the carrier can be subjected to sterilization by heat, pressure and medicine. For example, the highly porous glass carrier and fermentation starting liquid supplied into the reactor are concurrently sterilized by the application of heat and pressure, and then sterile-cultured yeast is supplied to the reactor. Therefore, immobilization of yeast and production of liquor can be conducted in desirable manner in view of sanitation.

TABLE 1

Glass compositions and Particle Diameter of Glass Powders

| Glass | Samples | Average particle diameter [μm] | Particle diameter deviation [μm] | $SiO_2$ | $Na_2O$ | $K_2O$ | CaO | MgO | $B_2O_3$ | $Al_2O_3$ | Remainder |
|---|---|---|---|---|---|---|---|---|---|---|---|
| Soda-lime glass | A-1 | 30 | 50 | 69.0 | 13.1 | 1.4 | 12.0 | 0.27 | — | 2.1 | 2.13 |
| | A-2 | | | | | | | | | | |
| | A-3 | 15 | 20 | | | | | | | | |
| Borosilicate glass | A-4 | 15 | 20 | 73.7 | 8.8 | — | 0.65 | — | 12.0 | 4.8 | 0.05 |

TABLE 2

Eluted Component Amount by Dealkali Treatment

| Dipping condition | | Sample No. | Eluted component [ppm] | | | | | Alkali component [ppm] | Non-alkalic component [ppm] |
|---|---|---|---|---|---|---|---|---|---|
| Temperature (°C.) | Time (hr) | | $SiO_2$ | $Na_2O$ | $K_2O$ | CaO | $Al_2O_3$ | | |
| 20 | 48 | A-1 | 36.5 | 49.3 | 2.3 | 2.1 | 0.1 | 53.7 | 36.6 |
| | | A-2 | 28.9 | 43.7 | 1.9 | 3.4 | 0.1 | 49.0 | 29.0 |
| | | A-3 | 83.2 | 77.5 | 3.4 | 2.4 | 0.2 | 83.3 | 83.4 |
| | | A-4 | 12.0 | 2.3 | 0.5 | 14.3 | 0.1 | 17.1 | 12.1 |
| 80 | 48 | A-1 | 203.1 | 147.4 | 7.7 | 3.1 | 2.2 | 158.2 | 205.3 |
| | | A-2 | 161.8 | 141.2 | 7.2 | 3.4 | 2.6 | 151.8 | 164.4 |
| | | A-3 | 325.1 | 261.9 | 10.8 | 1.0 | 3.6 | 273.7 | 328.7 |
| | | A-4 | 55.7 | 8.2 | 1.2 | 18.5 | 1.3 | 27.9 | 57.0 |
| 120 | 1 | A-1 | 141.0 | 149.9 | 7.6 | 1.2 | 3.9 | 158.7 | 144.9 |
| | | A-2 | 135.0 | 130.8 | 7.1 | 2.0 | 3.6 | 139.9 | 138.6 |
| | | A-3 | 233.3 | 237.6 | 9.7 | 0.3 | 4.2 | 247.6 | 237.5 |
| | | A-4 | 37.5 | 4.6 | 1.4 | 9.0 | 2.5 | 15.0 | 40.0 |

TABLE 3

(Example 1)

| | $SiO_2$ | $Al_2O_3$ | CaO | MgO | $K_2O$ | $Na_2O$ | $Fe_2O_3$ | MnO | $SO_3$ | Total |
|---|---|---|---|---|---|---|---|---|---|---|
| before dealkali treatment | 69.4 | 1.98 | 10.58 | 0.38 | 1.41 | 14.2 | 0.09 | 0.08 | 0.38 | 98.50% |
| after dealkali treatment | 70.8 | 2.00 | 10.33 | 0.35 | 1.38 | 13.2 | 0.10 | 0.08 | 0.27 | 98.51% |

TABLE 4

(Physical properties) (Example 1)

| | specific weight | weight in 1 container | specific gravity | moisture content ratio | strength |
|---|---|---|---|---|---|
| before dealkali treatment | 0.155 | 155 g | 0.26 | 10.2% | X = 9.52 kg<br>σ = 2.23 kg |
| after dealkali treatment | 0.148 | 148 g | 0.25 | 75.2% | X = 7.67 kg<br>σ = 2.29 kg |

TABLE 5

Glass Compositions (%) (Example 4)

| Kind of glass | $SiO_2$ | $Al_2O_3$ | CaO | MgO | $Na_2O$ | $Fe_2O_3$ | PbO | MnO | $B_2O_3$ | $SO_3$ |
|---|---|---|---|---|---|---|---|---|---|---|
| Soda-lime glass | 69.0 | 2.05 | 12.0 | 0.35 | 13.5 | 0.08 | — | 0.09 | — | 0.23 BaO |

TABLE 5-continued

| Kind of glass | Glass Compositions (%) (Example 4) | | | | | | | | | |
|---|---|---|---|---|---|---|---|---|---|---|
| | SiO₂ | Al₂O₃ | CaO | MgO | Na₂O | Fe₂O₃ | PbO | MnO | B₂O₃ | SO₃ |
| Borosilicate glass | 69.5 | 4.5 | — | — | 9.5 | 0.03 | — | — | 13.0 | 1.25 |

TABLE 6

Physical Properties Before and After Dealkali Treatment (Example 4)

| | | | | | | | | |
|---|---|---|---|---|---|---|---|---|
| 1. Sample No. | 1-A | | 2-A | | 1-B | | 2-B | |
| 2. Particle diameter (mm) | 1.0 | | 3.0 | | 1.0 | | 3.0 | JIS mesh |
| 3. Kind of Glass | Soda-lime glass | | | | borosilicate glass | | | |
| 4. dealkali treatment | before | after | before | after | before | after | before | after |
| 5. apparent specific gravity | 0.62 | 0.58 | 0.40 | 0.38 | 0.62 | 0.61 | 0.66 | 0.64 pycnometer |
| 6. moisture content ratio | 29.2 | 72.5 | 34.6 | 76.3 | 14.2 | 52.1 | 13.5 | 54.9 under vacuum for 10 minutes and then dipped |
| 7. median pore diameter | 2.6 | 11.6 | 6.0 | 18.1 | 0.11 | 4.16 | 0.06 | 12.36 Shimazu's poresizer No. 9305 |
| 8. pore volume (ml/g) | 1.35 | 1.44 | 2.07 | 2.29 | 1.08 | 1.21 | 0.92 | 1.18 Shimazu's poresizer No. 9305 |

TABLE 7

Physical properties of multi-cellular glass used in water retaining test (Example 5)

| No. | grains | grain diameter (mm) | apparent specific gravity | moisture content ratio (vol %) | porosity (vol %) | pore volume (ml/g) | specific surface area (m²/g) | median pore diameter (μ) |
|---|---|---|---|---|---|---|---|---|
| E | multi cellular glass grain | 5.0 | 0.16 | 82.6 | 92.6 | 5.79 | 6.25 | 39.51 |
| F | " | " | 0.26 | 79.4 | 88.3 | 3.40 | 5.70 | 21.71 |
| G | " | " | 0.36 | 48.8 | 83.3 | 2.35 | 49.17 | 13.35 |
| H | " | " | 0.37 | 13.3 | 81.1 | 1.98 | 58.30 | 0.43 |
| I | clay ball | " | 1.28 | 39.8 | 46.2 | 0.39 | 17.83 | 1.46 |

TABLE 8

Physical properties of multi-cellular glass grain used in water retaining test (Example 6)

| No. | grains | grain diameter (mm) | apparent specific gravity | moisture content ratio (vol %) | porosity (vol %) | pore volume (ml/g) | specific surface area (m²/g) | median pore diameter (μ) |
|---|---|---|---|---|---|---|---|---|
| M | multi cellular glass grain | 5.0 | 0.67 | 29.9 | 70.9 | 1.06 | 48.98 | 1.17 |
| N | " | " | 0.31 | 67.2 | 86.0 | 2.78 | 55.73 | 2.43 |
| O | " | " | 0.39 | 72.2 | 81.3 | 2.08 | 33.92 | 18.47 |
| P | " | " | 0.61 | 42.2 | 72.6 | 1.19 | 31.62 | 8.23 |
| Q | chamotte | " | 1.01 | 37.7 | 55.7 | 0.55 | 30.05 | 2.31 |
| R | anthracite | " | 1.28 | 4.4 | 18.6 | 0.15 | 20.83 | 20.83 |
| S | chemical bacteriological filter | " | 1.51 | 27.6 | 41.5 | 0.27 | 1.64 | 1.64 |

TABLE 9

Physical properties of soda-lime glass (3.0 mm grain diameter) (Example 7)

| 0. Sample | 1. Pore volume [V] (ml/g) | 2. Specific Surface area [S] (m²/g) | 3. Median pore diameter (μ) | 4. Average pore diameter [4V/S] (μ) | 5. Apparent specific gravity | 6. Porosity (%) | 7. Moisture content ratio (%) | 8. Specific gravity in water | 9. Apparent specific gravity in water | Condition of dealkali treatment of Sample S-1 |
|---|---|---|---|---|---|---|---|---|---|---|
| S-1 | 2.50 | 50.6 | 0.82 | 0.197 | 0.34 | 85.0 | 13.6 | 0.394 | 0.476 | Before dealkali treatment |
| S-2 | 2.47 | 37.6 | 1.05 | 0.263 | 0.34 | 84.0 | 17.2 | 0.411 | 0.512 | Dipping in hot water having temp. of 80° C. for 4 hours |
| S-3 | 2.50 | 35.4 | 1.51 | 0.283 | 0.35 | 84.5 | 22.5 | 0.445 | 0.575 | Dipping in hot water having temp. of 80° C. for 5 hours |
| S-4 | 2.56 | 33.3 | 2.97 | 0.308 | 0.33 | 84.5 | 30.4 | 0.474 | 0.634 | Dipping in hot water having temp. of 80° C. for 6 hours |
| S-5 | 2.48 | 31.2 | 6.60 | 0.318 | 0.36 | 84.1 | 44.6 | 0.650 | 0.806 | Dipping in 3% of Na₂CO₃ solution having temp. of 80° C. for 3 hours |
| S-6 | 2.57 | 19.9 | 10.40 | 0.517 | 0.33 | 84.8 | 60.4 | 0.833 | 0.934 | Dipping in 1.5% of NaOH solution having temp. of 80° C. for 3 hours |

TABLE 9-continued

Physical properties of soda-lime glass (3.0 mm grain diameter) (Example 7)

| 0. Sample | 1. Pore volume [V] (ml/g) | 2. Specific Surface area [S] (m²/g) | 3. Median pore diameter (μ) | 4. Average pore diameter [4V/S] (μ) | 5. Apparent specific gravity | 6. Porosity (%) | 7. Moisture content ratio (%) | 8. Specific gravity in water | 9. Apparent specific gravity in water | Condition of dealkali treatment of Sample S-1 |
|---|---|---|---|---|---|---|---|---|---|---|
| S-7 | 2.51 | 16.8 | 15.97 | 0.598 | 0.34 | 85.3 | 71.8 | 1.206 | 1.058 | Dipping in 3% of Na₂CO₃ solution having temp. of 80° C. for 6 hours |
| S-8 | 2.57 | 8.2 | 16.92 | 1.254 | 0.33 | 84.8 | 76.3 | 1.392 | 1.093 | Dipping in 1.5% of NaOH solution having temp. of 80° C. for 6 hours |

TABLE 10

Physical properties of soda-lime glass (3.0 mm grain diameter) (Example 8)

| 0. Sample | 1. Pore volume [V] (ml/g) | 2. Specific Surface area [S] (m²/g) | 3. Median pore diameter (μ) | 4. Average pore diameter [4V/S] (μ) | 5. Apparent specific gravity | 6. Porosity (%) | 7. Moisture content ratio (%) | 8. Specific gravity in water | 9. Apparent specific gravity in water | Condition of dealkali treatment of Sample $B_1$-1 |
|---|---|---|---|---|---|---|---|---|---|---|
| $B_1$-1 | 1.56 | 170.3 | 0.10 | 0.037 | 0.45 | 71.8 | 6.5 | 0.492 | 0.525 | Before dealkali treatment |
| $B_1$-2 | 1.55 | 141.5 | 0.15 | 0.044 | 0.45 | 69.8 | 9.7 | 0.498 | 0.547 | Dipping in hot water having temp. of 130° C. for 4 hours |
| $B_1$-3 | 1.66 | 120.4 | 0.55 | 0.055 | 0.43 | 71.4 | 16.9 | 0.517 | 0.599 | Dipping in hot water having temp. of 130° C. for 8 hours |
| $B_1$-4 | 1.65 | 36.9 | 2.09 | 0.179 | 0.44 | 72.6 | 36.5 | 0.693 | 0.805 | Dipping in hot water having temp. of 130° C. for 12 hours |
| $B_1$-5 | 1.52 | 25.3 | 2.61 | 0.240 | 0.46 | 69.9 | 43.1 | 0.808 | 0.891 | Dipping in 3% of Na₂CO₃ solution having temp. of 130° C. for 4 hours |
| $B_1$-6 | 1.61 | 19.2 | 3.51 | 0.335 | 0.45 | 72.5 | 49.5 | 0.891 | 0.945 | Dipping in 1.5% of NaOH solution having temp. of 130° C. for 3 hours |
| $B_1$-7 | 1.57 | 15.8 | 4.90 | 0.398 | 0.46 | 72.2 | 59.3 | 1.139 | 1.053 | Dipping in 3% of Na₂CO₃ solution having temp. of 130° C. for 8 hours |
| $B_1$-8 | 1.62 | 13.6 | 5.95 | 0.476 | 0.45 | 72.9 | 63.0 | 1.216 | 1.080 | Dipping in 1.5% of NaOH solution having temp. of 130° C. for 6 hours |

TABLE 11

Physical properties of soda-lime glass (2.0 mm grain diameter) (Example 9)

| 0. Sample | 1. Pore volume [V] (ml/g) | 2. Specific Surface area [S] (m²/g) | 3. Median pore diameter (μ) | 4. Average pore diameter [4V/S] (μ) | 5. Apparent specific gravity | 6. Porosity (%) | 7. Moisture content ratio (%) | 8. Specific gravity in water | 9. Apparent specific gravity in water | Condition of dealkali treatment of Sample $B_2$-1 |
|---|---|---|---|---|---|---|---|---|---|---|
| $B_2$-1 | 0.88 | 64.5 | 0.30 | 0.0545 | 0.73 | 64.2 | 12.8 | 0.837 | 0.858 | Before dealkali treatment |
| $B_2$-2 | 0.86 | 48.3 | 1.03 | 0.0712 | 0.75 | 64.5 | 27.6 | 1.036 | 1.026 | Dipping in hot water having temp. of 130° C. for 4 hours |
| $B_2$-3 | 0.92 | 45.0 | 1.30 | 0.0821 | 0.73 | 67.5 | 29.9 | 1.041 | 1.029 | Dipping in hot water having temp. of 130° C. for 5 hours |
| $B_2$-4 | 0.94 | 37.4 | 1.67 | 0.1004 | 0.71 | 66.7 | 32.1 | 1.046 | 1.031 | Dipping in hot water having temp. of 130° C. for 6 hours |
| $B_2$-5 | 0.92 | 34.6 | 2.18 | 0.1064 | 0.72 | 66.2 | 34.7 | 1.103 | 1.067 | Dipping in 3% of Na₂CO₃ solution having temp. of 130° C. for 3 hours |
| $B_2$-6 | 0.93 | 32.9 | 3.98 | 0.1106 | 0.74 | 67.3 | 43.2 | 1.303 | 1.172 | Dipping in 3% of |

TABLE 11-continued

Physical properties of soda-lime glass (2.0 mm grain diameter)
(Example 9)

| 0. Sample | 1. Pore volume [V] (ml/g) | 2. Specific Surface area [S] (m²/g) | 3. Median pore diameter (μ) | 4. Average pore diameter [4V/S] (μ) | 5. Apparent specific gravity | 6. Porosity (%) | 7. Moisture content ratio (%) | 8. Specific gravity in water | 9. Apparent specific gravity in water | Condition of dealkali treatment of Sample B₂-1 |
|---|---|---|---|---|---|---|---|---|---|---|
| B₂-7 | 0.89 | 31.6 | 8.23 | 0.1127 | 0.73 | 65.0 | 53.4 | 1.524 | 1.264 | Na₂CO₃ solution having temp. of 130° C. for 5 hours Dipping in 2% of NaOH solution having temp. of 130° C. for 5 hours |

TABLE 12

Physical properties of soda-lime glass microcarrier (grain diameter of 350 to 500 μm)
(Example 10)

| 0. Sample | 1. Pore volume [V] (ml/g) | 2. Specific Surface area [S] (m²/g) | 3. Median pore diameter (μ) | 4. Average pore diameter [4V/S] (μ) | 5. Apparent specific gravity | 6. Porosity (%) | 7. Moisture content ratio (%) | 8. Specific gravity in water | 9. Apparent specific gravity in water | Condition of dealkali treatment of Sample M-1 |
|---|---|---|---|---|---|---|---|---|---|---|
| M-1 | 1.10 | 42.4 | 3.60 | 3.60 | 0.63 | 69.3 | 21.2 | 0.800 | 0.842 | Before dealkali treatment |
| M-2 | 1.06 | 23.8 | 4.82 | 4.82 | 0.66 | 70.0 | 27.0 | 0.904 | 0.930 | Dipping in hot water having temp. of 80° C. for 5 hours |
| M-3 | 1.10 | 24.3 | 5.21 | 5.21 | 0.65 | 71.5 | 30.5 | 0.935 | 0.955 | Dipping in hot water having temp. of 80° C. for 8 hours |
| M-4 | 1.09 | 22.1 | 6.24 | 6.21 | 0.64 | 69.8 | 32.5 | 0.948 | 0.965 | Dipping in hot water having temp. of 120° C. for 1 hour |
| M-5 | 1.10 | 21.4 | 7.74 | 7.74 | 0.64 | 70.4 | 41.5 | 1.094 | 1.055 | Dipping in 2% of Na₂CO₃ solution having temp. of 80° C. for 5 hours |
| M-6 | 1.02 | 21.0 | 9.10 | 9.10 | 0.67 | 68.3 | 47.8 | 1.284 | 1.148 | Dipping in 2% of Na₂CO₃ solution having temp. of 80° C. for 8 hours |
| M-7 | 1.08 | 25.7 | 9.73 | 9.73 | 0.65 | 70.2 | 50.1 | 1.303 | 1.151 | Dipping in 4% of Na₂CO₃ solution having temp. of 80° C. for 5 hours |
| M-8 | 1.06 | 23.5 | 10.57 | 10.57 | 0.66 | 70.0 | 55.0 | 1.467 | 1.210 | Dipping in 4% of Na₂CO₃ solution having temp. of 80° C. for 8 hours |
| M-9 | 1.12 | 12.5 | 11.95 | 11.95 | 0.63 | 70.6 | 63.3 | 1.717 | 1.263 | Dipping in 2% of Na₂CO₃ solution having temp. of 120° C. for 1 hours |
| M-10 | 1.10 | 6.0 | 13.38 | 13.38 | 0.65 | 71.5 | 67.5 | 2.000 | 1.325 | Dipping in 4% of Na₂CO₃ solution having temp. of 120° C. for 1 hours |

TABLE 13

Physical properties of soda-lime glass (3.0 mm grain diameter)
(Example 11)

| 0. Sample | 1. Pore volume [V] (ml/g) | 2. Specific Surface area [S] (m²/g) | 3. Median pore diameter (μ) | 4. Average pore diameter [4V/S] (μ) | 5. Apparent specific gravity | 6. Porosity (%) | 7. Moisture content ratio (%) | 8. Specific gravity in water | 9. Apparent specific gravity in water | Condition of dealkali treatment of Sample S₂-0 |
|---|---|---|---|---|---|---|---|---|---|---|
| S₂-O | 1.48 | 57.0 | 0.27 | 0.103 | 0.50 | 75.5 | 8.0 | 0.554 | 0.590 | Before dealkali treatment |
| S₂-A | 1.56 | 23.9 | 11.45 | 0.261 | 0.48 | 74.9 | 69.7 | 1.584 | 1.177 | Dipping in 5% of Na₂CO₃ solution having temp. of 80° C. for 12 hours |
| S₂-B | 1.47 | 28.8 | 1.25 | 0.204 | 0.50 | 73.5 | 19.5 | 0.621 | 0.695 | Dipping in 5% of HCl solution having temp. of 80° C. for 12 hours |
| S₂-C | 1.52 | 44.0 | 8.55 | 0.138 | 0.49 | 74.5 | 59.1 | 1.198 | 1.081 | Dipping in hot water |

TABLE 13-continued

Physical properties of soda-lime glass (3.0 mm grain diameter)
(Example 11)

| 0. Sample | 1. Pore volume [V] (ml/g) | 2. Specific Surface area [S] (m²/g) | 3. Median pore diameter (μ) | 4. Average pore diameter [4V/S] (μ) | 5. Apparent specific gravity | 6. Porosity (%) | 7. Moisture content ratio (%) | 8. Specific gravity in water | 9. Apparent specific gravity in water | Condition of dealkali treatment of Sample $S_2$-0 |
|---|---|---|---|---|---|---|---|---|---|---|
| | | | | | | | | | | having temp. of 80° C. for 12 hours |

TABLE 14

(Example 12)

| | Sample No. | | | | | | | |
|---|---|---|---|---|---|---|---|---|
| | 1 | 2 | 3 | 4 | 5 | 6 | 7 | 8 |
| grain diameter (mm) | 6.0 | 4.0 | 2.0 | 4.0 | 4.0 | 15.0 | 4.0 | 5.0 |
| bulk specific gravity | 0.17 | 0.20 | 0.30 | 0.22 | 0.20 | 0.08 | 0.18 | 0.15 |
| absolute specific gravity | 0.32 | 0.30 | 0.44 | 0.44 | 0.35 | 0.14 | 0.31 | 0.28 |
| moisture content ratio (%) | 79.7 | 80.4 | 75.0 | 73.7 | 74.9 | 92.2 | 82.4 | 82.6 |
| compression strength (kg) | 11.9 | 2.70 | 1.80 | 1.81 | 4.8 | — | 1.6 | 2.2 |
| pore volume (ml/g) | 1.76 | 3.28 | 2.63 | 1.92 | 3.30 | 5.29 | 3.3 | 3.7 |
| porous surface area (m²/g) | 13.0 | 3.20 | 35.4 | 2.97 | 50.0 | 0.73 | 14.4 | 2.2 |
| median pore diameter (μm) | 13.2 | 25.1 | 6.49 | 37.5 | 2.00 | 40.2 | 20.7 | 24.0 |

TABLE 15 yeast cell numbers immobilized in multi-cellular glass grain
(Example 12)

| glass samples | No. 1 | No. 2 | No. 3 | No. 4 | No. 5 | No. 6 | No. 7 | No. 8 |
|---|---|---|---|---|---|---|---|---|
| yeast cell number in unit volume *1 (cells/ml) | $2.6 \times 10^7$ | $1.5 \times 10^8$ | $1.0 \times 10^8$ | $6.6 \times 10^8$ | $3.0 \times 10^7$ | $1.5 \times 10^8$ | $1.0 \times 10^7$ | $1.3 \times 10^7$ |
| yeast cell number in unit surface area *2 (Cells/cm²) | $2.6 \times 10^6$ | $1.0 \times 10^7$ | $3.3 \times 10^6$ | $4.4 \times 10^7$ | $2.0 \times 10^6$ | $3.8 \times 10^7$ | $6.7 \times 10^6$ | $3.3 \times 10^6$ |
| yeast cell number in unit weight *3 (cells/g) | $8.1 \times 10^7$ | $5.0 \times 10^8$ | $2.3 \times 10^8$ | $1.5 \times 10^9$ | $8.6 \times 10^7$ | $1.1 \times 10^9$ | $3.2 \times 10^7$ | $4.6 \times 10^7$ |
| yeast desorption ratio *4 (%) | — | — | — | — | — | — | 0 | 0 |

TABLE 16 batch type beer brewage by yeast carrying carrier
(Example 12)

| alcohol density (w/w %) | 3.22 |
|---|---|
| extract (°P) | 3.27 |
| α-aminate nitrogen (mg/100 ml) | 7.20 |

TABLE 17 cortinuous beer brewage by yeast carrying carrier
(Example 12)

| alcohol density (w/w %) | 3.22 |
|---|---|
| extract (°P) | 3.32 |
| α-aminate nitrogen (mg/100 ml) | 10.0 |

TABLE 18

(Example 13)

| grain | No. 9 | No. 10 |
|---|---|---|
| diameter | 3.0 | 5.0 |
| bulk specific gravity | 0.29 | 0.31 |
| apparent specific gravity | 0.53 | 0.54 |
| moisture content ratio (%) | 59.1 | 50.0 |
| compression strength (kg) | 2.5 | — |
| pore volume * (ml/g) | 1.27 | 1.48 |
| porous surface area * (m²/g) | 38.2 | 37.0 |
| median porediameter * (μm) | 3.26 | 8.2 |

TABLE 19 cell number of Zymomonas mobilis immobilized in glass carrier
(Example 13)

| Samples | No. 9 | No. 10 |
|---|---|---|
| cell number in unit volume (cells/ml) * | $3.9 \times 10^9$ | $2.8 \times 10^9$ |
| cell number in unit surface area (cells/cm²) * | $1.9 \times 10^8$ | $2.3 \times 10^8$ |
| cell number in unit weight (cells/g) * | $7.4 \times 10^9$ | $5.2 \times 10^9$ |

While the invention has been described in detail and with reference to specific embodiments thereof, it will be apparent for those skilled in the art that various changes and modifications can be made therein without departing from the spirit and scope of the invention.

What is claimed is:

1. A method of producing a granular multi-cellular glass comprising the steps of:
preparing a multi-cellular glass grain having a surface layer and internal cell walls formed therein micropores with a given size, said glass grain being provided with a given moisture content ratio, said preparing step comprising the steps of pulverizing a starting non-phase separated glass material, adding a foaming agent to said pulverized glass material to provide a mixture of the pulverized glass material and said foaming agent, granulating said mixture to provide granulations, and heating said granulations at a temperature from 800° to 1000° C.

to activate the foaming agent without phase-separation of the glass;

dipping said multi-cellular glass grain in one of water and alkali solution having a temperature of at least 70° C. for at least 3 hours while adjusting and maintaining at least one of parameters of temperature of one of said water and said alkali solution, pH of said alkali solution, and period of said dipping; and eluting primarily soluble alkali component from said surface layer and said cell walls so as to form new micropores in the layer and cell walls for communicating the respective said cells and to increase the pore size of said micropores already formed to thereby control a change of said moisture content ratio of said multi-cellular glass grain in range more than 50% so that at least one of median pore diameter ranges from 1 to 50 μm and specific gravity ranges from 0.9 to 1.3 of said multi-cellular glass grain is controlled at a desired level.

2. A method for producing a granular multi-cellular glass comprising the steps of:

preparing a non-phase separated multi-cellular glass grain by employing a glass having selected particle diameter, in consideration of a group of graphical curves, each showing the relationship between a specific gravity and a median pore diameter of glass particles, from which specific gravity in range of 0.9 to 1.3 and median pore diameter in range of 1 to 50 μm of a final granular multi-cellular glass are determined and a curve passing through the determined point and being analogous with said group of curves is delineated and by heating said selected multi-cellular glass grain without phase-separation at a condition the same as that in the production of glasses which constitute said group of curves, said multi-cellular glass grain having a surface layer and cell walls;

dipping said prepared multi-cellular glass grain in one of water and alkali solution having a temperature of at least 70° C. for at least 3 hours while adjusting and maintaining at least one of parameters of temperature of one of said water and said alkali solution, pH of said alkali solution, and period of said dipping; and eluting alkali component from said surface layer and said cell walls, whereby said desirable specific gravity and median pore diameter are simultaneously obtained in said final granular multi-cellular glass.

3. A granular multi-cellular glass essentially consisting of a multi-cellular glass grain having a surface layer and an internal cell structure defined by a plurality of cell walls, said surface layer and cell walls being formed with micropores and pinholes which allow liquid to pass therethrough, each of said micropores having a median pore diameter ranging 1.0 to 50 μm, and a pore volume of said micropores ranging from 1.0 to 5.0 ml/g, whereby said glass has a moisture content ratio more than 50%, said granular multi-cellular glass produced by the steps of preparing a multi-cellular glass grain having a surface layer and internal cell walls formed therein micropores with a given size, said glass grain being provided with a given moisture content ratio, said preparing step comprising the steps of pulverizing a starting non-phase separated glass material, adding a foaming agent to said pulverized glass material to provide a mixture thereof, granulating said mixture to provide granulations, and heating said granulations at a temperature of from 800° to 1000° C. to activate the foaming agent without phase-separation of the glass; dipping said multi-cellular glass grain in one of water and alkali solution having a temperature of at least 70° C. for at least 3 hours; and eluting primarily soluble alkali component from said surface layer and said cell walls to form new micropores for communicating the respective said cells and to increase the pore size of said micropores already formed, whereby a granular multi-cellular glass having increased moisture content ratio ranges more than 50% is provided.

4. The granular multi-cellular glass as defined in claim 3, wherein during the dipping at least one of temperature of one of said water and said alkali solution, pH of said alkali solution and period of said dipping is adjusted and maintained for controlling a change of said moisture content ratio in range more than 50% by eluting primarily soluble alkalic component from said surface layer and said cell walls, so that said multi-cellular glass grain obtains at least one of median pore diameter ranges from 1.0 to 50 μm and specific gravity ranges fro. 0.9 to 1.3 to be controlled thereby.

5. A microcarrier for immobilizing microbe therein essentially consisting of a granular multi-cellular glass having a surface layer and an internal cell structure defined by a plurality of cell walls being formed with micropores and pinholes which allow microbe to pass therethrough and have a median pore diameter ranges from 1.0 to 50 μm, and a pore volume ranges from 1.0 to 5.0 ml/g and said granular multi-cellular glass having a moisture content ratio more than 50%, said granular multi-cellular glass produced by the steps of preparing a multi-cellular glass grain having a surface layer and internal cell walls formed therein micropores with a given size, said glass grain being provided with a given moisture content ratio, said preparing step comprising the steps of pulverizing a starting non-phase separated glass material, adding a foaming agent to said pulverized glass material to provide a mixture of the pulverized glass material and said foaming agent, granulating said mixture to provide granulations, and heating said granulations at a temperature of from 800° to 1000° C. to activate said foaming agent without phase-separation of the glass; dipping said multi-cellular glass grain in one of water and alkali solution having a temperature of at least 70° C. for at least 3 hours; and eluting primarily soluble alkali component from said surface layer and said cell walls to form new micropores for communicating the respective said cells and to increase the pore size of said micropores already formed in said surface layer and said cell walls, whereby a granular multi-cellular glass having increased moisture content ratio ranges more than 50% is provided.

6. The microcarrier as defined in claim 5, wherein said granular multi-cellular glass has a grain diameter ranging from 0.5 to 15 μm.

* * * * *